(12) United States Patent
Hu et al.

(10) Patent No.: US 12,295,992 B2
(45) Date of Patent: May 13, 2025

(54) USE OF ALDH1A AND AGONIST, CATALYST AND INHIBITOR THEREOF

(71) Applicant: SHANGHAI INSTITUTES FOR BIOLOGICAL SCIENCES, CHINESE ACADEMY OF SCIENCES, Shanghai (CN)

(72) Inventors: Ronggui Hu, Shanghai (CN); Xingxing Xu, Shanghai (CN); Xiaobo Gao, Shanghai (CN); Chuanyin Li, Shanghai (CN); Zijian Hao, Shanghai (CN)

(73) Assignee: Center for Excellence in Molecular Cell Science, Chinese Academy of Sciences, Shanghai (CN)

( * ) Notice: Subject to any disclaimer, the term of this patent is extended or adjusted under 35 U.S.C. 154(b) by 1250 days.

(21) Appl. No.: 16/495,863

(22) PCT Filed: Mar. 21, 2018

(86) PCT No.: PCT/CN2018/079758
§ 371 (c)(1),
(2) Date: Apr. 27, 2020

(87) PCT Pub. No.: WO2018/171616
PCT Pub. Date: Sep. 27, 2018

(65) Prior Publication Data
US 2020/0268855 A1    Aug. 27, 2020

(30) Foreign Application Priority Data

Mar. 21, 2017  (CN) .......................... 201710170558.8

(51) Int. Cl.
| | | |
|---|---|---|
| *A61K 38/44* | (2006.01) | |
| *A61K 31/203* | (2006.01) | |
| *A61K 31/357* | (2006.01) | |
| *A61K 31/4164* | (2006.01) | |
| *A61K 31/4184* | (2006.01) | |
| *A61K 31/428* | (2006.01) | |
| *A61K 31/44* | (2006.01) | |
| *A61K 31/47* | (2006.01) | |
| *A61K 31/496* | (2006.01) | |
| *A61P 25/00* | (2006.01) | |

(52) U.S. Cl.
CPC ............ *A61K 38/44* (2013.01); *A61K 31/203* (2013.01); *A61K 31/357* (2013.01); *A61K 31/4164* (2013.01); *A61K 31/4184* (2013.01); *A61K 31/428* (2013.01); *A61K 31/44* (2013.01); *A61K 31/47* (2013.01); *A61K 31/496* (2013.01); *A61P 25/00* (2018.01)

(58) Field of Classification Search
CPC .... A61K 38/44; A61K 31/203; A61K 31/357; A61K 31/4164; A61K 31/4184; A61K 31/428; A61K 31/44; A61K 31/47; A61K 31/496; A61K 31/11; A61K 31/192; A61K 31/343; A61K 31/4174; A61K 31/4402; A61K 31/4436; A61K 45/06; A61K 31/07; A61K 45/00; A61P 25/00; G01N 2500/00; G01N 21/6486; G01N 2800/30; Y02A 50/30; C12Q 1/32; C12Q 1/66
See application file for complete search history.

(56) References Cited

U.S. PATENT DOCUMENTS

| | | | | |
|---|---|---|---|---|
| 2,369,158 | A | * | 2/1945 | Milas .................... C07C 403/20 560/126 |
| 2004/0092589 | A1 | | 5/2004 | Neumann |
| 2016/0257957 | A1 | * | 9/2016 | Greenberg ......... A61K 31/4525 |

FOREIGN PATENT DOCUMENTS

WO    WO-2011109398 A2 *  9/2011   ........... A61K 31/198

OTHER PUBLICATIONS

Jason J. Yi, et al., "An Autism-Linked Mutation Disables Phosphorylation Control of UBE3A", CellPress, 2015, Cell 162, pp. 1-18.
K Xia, et al., "Common genetic variants on 1p13.2 associate with risk of autism", Molecular Psychiatry (2014) 19, 1212-1219.
Tianyun Wang, et al., "De novo genic mutations among a Chinese autism spectrum disorder cohort", Nature Communications, 7:13316, DOI: 10.1038/ncomms13316, Published Nov. 8, 2016, pp. 1-10.
Caroline Nava, et al., "Prospective diagnostic analysis of copy number variants using SNP microarrays in individuals with autism spectrum disorders", European Journal of Human Genetics (2014) 22, pp. 71-78.
Jianming Xu, "Preparation, Culture, and Immortalization of Mouse Embryonic Fibroblasts", Current Protocols in Molecular Biology (2005) pp. 28.1.1-28.1.8.
Jason Aoto, et al., "Synaptic Signaling by All-Trans Retinoic Acid in Homeostatic Synaptic Plasticity", CellPress, Neuron 60, pp. 308-320, Oct. 23, 2008.
Maureen A. Kane, et al., "Quantification of Endogenous Retinoids", Methods in Molecular Biology 652, DOI 10.1007/978-1-60327-325-1_1, pp. 1-54.

(Continued)

*Primary Examiner* — Aaron J Kosar
(74) *Attorney, Agent, or Firm* — Adam Warwick Bell; Matthew Rupert Kaser

(57) ABSTRACT

Disclosed is the use of ALDH1A and an agonist, a catalysate and an inhibitor thereof. In particular, disclosed is the use of ALDH1A or an agonist thereof, or a catalysate thereof in the preparation of a pharmaceutical composition or a formulation for the treatment and/or prevention of autism.

6 Claims, 9 Drawing Sheets
Specification includes a Sequence Listing.

(56) References Cited

OTHER PUBLICATIONS

Yehezkel Sztainberg, et al., "Reversal of phenotypes in MECP2 duplication mice using genetic rescue or antisense oligonucleotides", Nature, Letters, doi:10.1038/nature16159, pp. 1-17.
Joseph T. Glessner, et al. "Autism genome-wide copy number variation reveals ubiquitin and neuronal genes", Nature, Letters vol. 459, May 28, 2009, doi:10.1038/nature07953, pp. 569-573.
Tal Keren-Kaplan, et al., "Synthetic biology approach to reconstituting the ubiquitylation cascade in bacteria", The EMBO Journal (2012) vol. 31, pp. 378-390.
Sushant Kumar, et al., "Identification of HHR23A as a Substrate for E6-associated Protein-mediated Ubiquitination", The Journal of Biological Chemistry, vol. 274, No. 26, Issue of Jun. 25, pp. 18785-18792, 1999.
Daphna Zaaroor-Regev, et al., "Regulation of the polycomb protein Ring1B by selfubiquitination or by E6-AP may have implications to the pathogenesis of Angelman syndrome", PNAS, vol. 107, No. 15. pp. 6788-6793, Apr. 13, 2010.
Tina Ansari, et al., "Peptide Interactions Stabilize and Restructure Human Papillomavirus Type 16 E6 To Interact with p53", Journal of Virology, Oct. 2012, vol. 86, No. 20, pp. 11386-11391.
Robert W. Storms, et al., "Isolation of primitive human hematopoietic progenitors on the basis of aldehyde dehydrogenase activity", Proc. Natl. Acad. Sci. USA, vol. 96, pp. 9118-9123, Aug. 1999.
Lu Chen, et al., "Synaptic retinoic acid signaling and homeostatic synaptic plasticity", Neuropharmacology 78 (2014) pp. 3-12.
Edward B. Han, et al., "Development regulates a switch between postand presynaptic strengthening in response to activity deprivation", PNAS, Jun. 30, 2009, vol. 106, No. 26, pp. 10817-10822.
Rich Stoner, et al., "Patches of Disorganization in the Neocortex of Children with Autism", The New England Journal of Medicine, 370;13, Mar. 27, 2014, pp. 1209-1219.
Maggie L. Chow, et al., "Age-Dependent Brain Gene Expression and Copy Number Anomalies in Autism Suggest Distinct Pathological Processes at Young Versus Mature Ages", PLoS Genetics, Mar. 2012, vol. 8, Issue 3, e1002592, pp. 1-14.
Mary Anne Anderson, et al., "Use of Cyclosporin a in Establishing Epstein-Barr Virus-Transformed Human Lymphoblastoid Cell Lines", In Vitro vol. 20, No. 11, Nov. 1984, pp. 856-858.

* cited by examiner

USE OF ALDH1A AND AGONIST, CATALYST AND INHIBITOR THEREOF

TECHNICAL FIELD

The present invention belongs to field of biotechnology, and in particular, relates to use of ALDH1A and agonist, catalysate and inhibitor thereof.

STATEMENT FOR THE SEQUENCE LISTING

A sequence listing text (.txt) file is submitted herewith under 37 CFR. 1.821 (c) and is hereby incorporated by reference in its entirely. The details of the file as required under 37 CFR. 1.52 (e) (5) and 37 CFR 1.77 (b) (5) are as follows: Name of file is P2019-1504XLB.txt; date of creation is Dec. 23, 2019; size is 4,096 bytes. The content of the sequence listing information recorded in computer readable form is identical to the written sequence listing (if any) and identical to the sequence information provided with the original filed application and with the priority application, and contains no new matter. The information recorded in electronic form (if any) submitted (under Rule 13ter, if appropriate) with this application is identical to the sequence listing as contained in the application as filed.

TECHNICAL BACKGROUND

Autism spectrum disorder, referred to as "autism", also known as "ASD", is a serious neural disorder of development and its core symptoms are social communication barriers, and repeated stereotypic behavior. Among the autism cases, a copy number variation (CNV) in chromosome 15q11-q13 accounts for 1-3%. This CNV can cause excessive activation of UBE3A E3 ubiquitin ligase, but its specific mechanism of pathogenesis is unclear.

Autism spectrum disorder is an extensive neural disorder of development having various pathogenic causes and the core symptoms thereof mainly comprises deficiency of capability for social communication, limited and repetitive interests, behaviors or activities and so on. To date, genetic factors that cause autism include point mutations and chromosome copy number variations, and their mutations encompass various affected genes, and involve different signaling pathways. Although the genetic factors that cause autism are very complex and diverse, autistic patients show similar core phenotypic symptoms, as well as disorder of synaptic homeostasis, suggesting a common mechanism of pathogenesis may exist in the disorder of autism. Therefore, it is particularly important and critical to clarify the molecular mechanism between genetic factors and synaptic homeostasis disorder in autism.

In autism cases, the CNV of 15q11-q13 in the maternal chromosome accounts for approximately 1-3%. It is discovered in the study of multi-population cases that E3 ubiquitin ligase UBE3A plays a major role for the symptoms of 15q11-q13 CNV. Further, in various transgenic mouse models, overexpression of UBE3A can also cause autism phenotype in mice. These results demonstrate that over-activation of UBE3A is the most clearly elucidated cause of autism subtype. In a recent report, a UBE3A point mutation highly associated with autism was discovered, and this point mutation blocked phosphorylation of UBE3A by protein kinase A (PKA), resulting in overactivation of UBE3A and increased synapse formation (Yi et al., 2015). A variety of substrates for E3 ubiquitin ligase UBE3A have now been reported, but it is still impossible to explain the mechanism for autism. Therefore, some other unknown substrate proteins that are dysfunctional may exist in the brains of autistic patients.

Therefore, there is an urgent need to develop a relevant application of ALDH1A and its agonist, catalysate and inhibitor via systematic screening of UBE3A substrates.

SUMMARY OF INVENTION

It is an object of the present invention to provide the use of ALDH1A and its agonists, catalysates and inhibitors.

In the first aspect of the invention there is provided a use of ALDH1A, or an agonist thereof, or a catalysate thereof, and/or a catalytic substrate thereof, in the preparation of a pharmaceutical composition or formulation for treatment and/or prevention of autism.

In another preferred embodiment, the ALDH1A agonist is not an inhibitor of UBE3A.

In another preferred embodiment, the "inhibitor that is not an inhibitor of UBE3A" means that the ALDH1A agonist has no or essentially no influence on the expression or activity of UBE3A (e.g., the ratio of expression E1 or activity A1 of UBE3A in the experimental group in which the ALDH1A agonist is present, to expression E0 or activity A0 of UBE3A in the blank control group in which the ALDH1A agonist is absent, (i.e., E1/E0 or A1/A0), is 0.7-1.3, preferably 0.8-1.2, more preferably 0.9-1.1).

In another preferred embodiment, the autism is autism in human population.

In another preferred embodiment, the population is a population having chromosome 15q11-q13 copy number amplification In another preferred embodiment, the population is a population having UBE3A overexpressed or overactivated.

In another preferred embodiment, the population is a population having a UBE3A with T508A mutation.

In another preferred embodiment, the ALDH1A is selected from the group consisting of ALDH1A1, ALDH1A2, ALDH1A3, and a combination thereof.

In another preferred embodiment, the agonist comprises an expression agonist, or a protein degradation inhibitor.

In another preferred embodiment, the ALDH1A agonist is selected from the group consisting of: N-(1,3-Benzodioxol-5-ylmethyl)-2,6-dichlorobenzamide, N-(1,3-Benzodioxol-5-ylmethyl)-2,6-dichlorobenzamide, 6-methyl-2-(phenylazo)-3-Pyridinol, 2-(benzo[d][1,3]dioxol-5-yl)-N-(5,6-dihydro-4H-cyclopenta[c]isoxazol-3-yl)acetamide, and derivatives thereof.

In the second aspect of the invention, it provides a use of retinoic acid or a retinoic acid analog, or a solvate thereof, or a pharmaceutically acceptable salt thereof, in the preparation of a pharmaceutical composition or formulation for the treatment and/or prevention of autism.

In another preferred embodiment, the retinoic acid analog is selected from the group consisting of: retinol, retinal, all-trans retinoic acid, 13-cis retinoic acid, 9-cis retinoic acid, acitretin, Avi A, adapalene, bexarotene, tazarotene, and combinations thereof.

In the third aspect of the invention, it provides a use of a starting compound for retinoic acid synthesis or an inhibitor of retinoic acid degradation enzyme in the preparation of a pharmaceutical composition or formulation for treatment and/or prevention of autism.

In another preferred embodiment, the inhibitor of retinoic acid degradation enzyme is selected from the group consisting of liarozole, ketoconazole, talarozole, and combinations thereof.

In the fourth aspect of the invention, it provides a use of an ALDH1A inhibitor in the preparation of a formulation for establishing an autistic animal model.

In another preferred embodiment, the ALDH1A inhibitor is selected from the group consisting of a small molecule compound, an antibody, a nucleic acid, and combinations thereof.

In another preferred embodiment, the ALDH1A inhibitor is a UBE3A agonist.

In another preferred embodiment, the nucleic acid is selected from the group consisting of miRNA, siRNA, sgRNA/Cas9 complex, and combinations thereof.

In another preferred embodiment, the ALDH1A inhibitor is selected from the group consisting of disulfiram, 4-(N,N-diethyl)aminobenzaldehyde (DEAB), WIN-18446, A37 (CM037), NCT-501 hydrochloride, CVT-10216, and combinations thereof.

In the fifth aspect of the invention, it provides a method for auxiliary diagnosis and/or prognosis of autism, which comprises the steps of:

(1) providing a sample to be tested, which is selected from the group consisting of blood and body fluid;

(2) detecting concentration, content, and/or activity of the marker;

(3) comparing with a standard value or a standard curve, thereby performing an auxiliary diagnosis and/or prognosis;

wherein the marker is selected from the group consisting of retinoic acid, ALDH1A, and combinations thereof.

In another preferred embodiment, in step (3), when the retinoic acid concentration in the sample is lower than that in a normal donor sample (8-20 nM), it indicates that the subject or patient is at higher risk of developing autism than that in the normal population or has a poor prognosis; and/or when the activity of ALDH1A in the sample is lower than that in the normal donor sample, it indicates that the patient has a higher risk of autism than that in the normal population or has a poor prognosis.

In the sixth aspect of the invention, it provides a method of assessing the risk of side effects of a substance to be tested, wherein the risk of side effects is a risk of inducing or triggering autism, and the method comprises the steps of:

(a) providing a substance to be tested;

(b) in the test group to which the substance to be tested is administered, determining the influence of the test substance on a test index; and in the control group to which the test substance is not administered, determining data of the same test index; wherein the test index is selected from the group consisting of: the level or concentration of retinoic acid, the amount or activity of ALDH1A expression, and combinations thereof;

(c) comparing the measurement result T of the test index in the test group with the measurement result C of the test index in the control group;

if the measurement result T is significantly lower than the measurement result C, it indicates that the substance to be test has a risk of causing side effect in a pregnant woman and/or an infant.

In another preferred embodiment, the substance to be tested is selected from the group consisting of a drug, a daily chemical, and combinations thereof.

In another preferred embodiment, the side effects include causing autism in the current generation, causing autism in the offspring, and combinations thereof.

In another preferred embodiment, said "significantly lower" means that the T/C ratio is less than 0.7 with a statistically significant difference $P<0.05$.

In another preferred embodiment, in step (b), the assay is carried out in an animal model or in a culture system.

In another preferred embodiment, the method further comprises verifying via animal experiments the substance to be tested which is indicated to has a side effect in step (c).

In the seventh aspect of the invention, it provides a pharmaceutical combination or a kit comprising the pharmaceutical combination, wherein the pharmaceutical combination comprises:

(a) a first pharmaceutical composition comprising a pharmaceutically acceptable carrier and a first active ingredient selected from the group consisting of clotrimazole, montelukast, and montelukast sodium; and (b) a second pharmaceutical composition comprising a pharmaceutically acceptable carrier and a second active ingredient selected from the group consisting of ALDH1A, an ALDH1A agonist, an ALDH1A catalysate, an ALDH1A catalytic substrate, and combinations thereof.

In another preferred embodiment, the second pharmaceutical composition is used to reduce the risk of side effects of the first pharmaceutical composition, which is a risk of inducing or triggering autism.

In the eighth aspect of the invention, it provides a pharmaceutical composition, which comprises:

(a) a first active ingredient selected from the group consisting of clotrimazole, montelukast, and montelukast sodium; and (b) a second active ingredient selected from the group consisting of ALDH1A, an ALDH1A agonist, an ALDH1A catalysate, an ALDH1A catalytic substrate, and combinations thereof.

In another preferred embodiment, the second active ingredient is used to reduce the risk of side effects of the first active ingredient, which is a risk of inducing or triggering autism.

In another preferred embodiment, the second pharmaceutically active ingredient is selected from the group consisting of retinoic acid and analogs thereof, retinoic acid degradation enzyme inhibitor, and combinations thereof.

In a ninth aspect of the invention, it provides a method of screening a drug candidate (or potential therapeutic agent) for treating or preventing autism, which comprises the steps of:

(a) providing a candidate substance to be tested;

(b) determining, in the test group to which the candidate substance to be tested is administered, the effect of the candidate substance to be tested on the test index; and in the control group to which the candidate substance to be tested is not administered, determining data of the same test index; wherein the test index is selected from the group consisting of: the level or concentration of retinoic acid, the amount or activity of ALDH1A expression, and combinations thereof;

(c) comparing the measurement result T of the test index in the test group with the measurement result C of the test index in the control group;

if the measurement result T is significantly higher than the measurement result C, it indicates that the candidate substance to be tested can be used as a drug candidate for treating or preventing autism.

In another preferred embodiment, said "significantly higher" means that the T/C ratio is greater than 1.2 with a statistically significant difference $P<0.05$.

In another preferred embodiment, in step (b), the assay is carried out in an animal model or in a culture system.

In another preferred embodiment, the method further comprises verifying via animal experiments the candidate substance which is indicated to be a drug candidate for treating or preventing autism in step (c).

In the tenth aspect of the invention, it provides a use of a polypeptide or an antibody or a compound capable of blocking the binding of UBE3A and an ALDH1A family protein in the preparation of a pharmaceutical composition or formulation for treatment and/or prevention of autism.

In another preferred embodiment, the polypeptide is selected from the group consisting of peptide-1, peptide-2, peptide-3.

It is to be understood that within the scope of the present invention, the various technical features of the present invention and the various technical features specifically described hereinafter (such as those in the examples) may be combined with each other to form a new or preferred technical solution, which is not repeatedly described one by one due to limitation of text.

DETAILED DESCRIPTION

Figure 1:
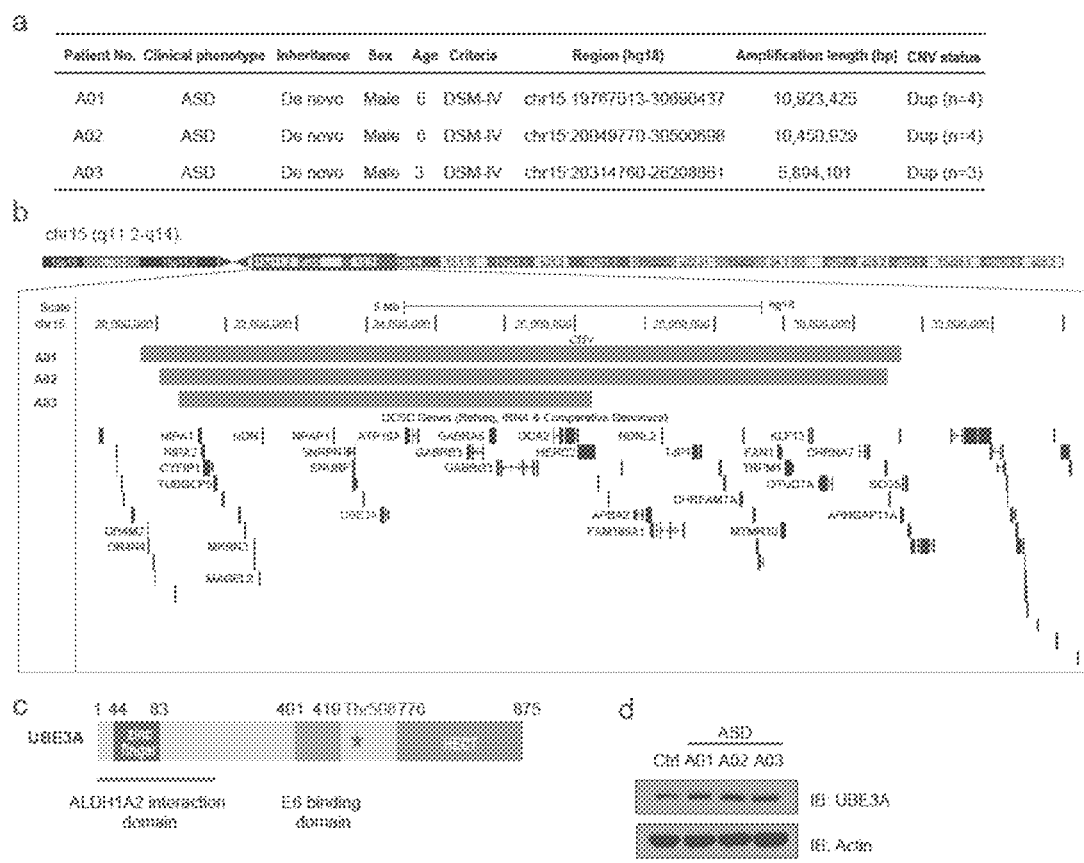
FIG. 1 shows the copy number amplification of chromosome 15q11.2-14 in a sample of autistic patients. (a) Copy number variation of the UBE3A region was observed in 3 ASD patients. (b) The repeated DNA regions (in blue) in 3 ASD patients were mapped onto the hg18 human genome using UCSC, wherein 15q11.2-q14 was marked in red box. The known genes are indicated at the bottom and the UBE3A gene is marked in red. (c) Schematic representation of the human UBE3A protein domain. (d) Static UBE3A protein levels in immortalized lymphocytes from patients with excessive UBE3A gene and from normal controls.

After extensive and intensive research, the inventors have firstly and unexpectedly discovered a new pathway associated with autism. For the first time, the inventors have discovered that the core protein in the pathway or the synthetase ALDH1A has a significant correlation with the occurrence of autism. By supplementing the synthetase ALDH1A, or an agonist thereof, or a synthetic product thereof, or a catalytic substrate thereof, it is helpful to prevent and ameliorate autism and symptoms associated with autism. The present invention is completed on this basis.

Specifically, it is shown in the experiments that the rate-limiting synthetase (ALDH1A2) of retinoic acid (RA) can be negatively regulated by UBE3A in a ubiquitin modification dependent manner. High dose or overactivation of the autism-associated UBE3A protein is capable of disrupting RA-mediated neuronal synaptic homeostasis. In a mouse animal model, overexpression of UBE3A protein in the prefrontal cortex (PFC) of the mouse brain and administration of an ALDH1A inhibitor can lead to the appearance of similar symptoms of autism in mice. By supplementing RA, the symptoms of mouse autism caused by UBE3A overexpression can be significantly ameliorated. These results suggest that the interference of the RA pathway is a potential mechanism for the association between over activation of UBE3A and phenotype of autism.

Retinoic Acid and its Derivatives

Retinoic acid and its derivatives are mainly divided into three generations: the first generation includes: retinol, retinal, tretinoin (all-trans-retinoic isotretinoin (13-cis-retinoic acid), alitretinoin (9-cis-retinoic acid); the second generation includes: etretinate, acitretin; and the third generation includes: adapalene, bexarotene, and tazarotene. (retinol, retinal, all-trans retinoic acid, 13-cis retinoic acid, 9-cis retinoic acid, etretinate, acitretin, adapalene, bexarotene, tazarotene)

The derivatives also include ester derivatives of the individual compounds which are hydrolyzed into the acid or salt form in vivo. Some of the compounds have the following structural formula:

1st generation of RA and its derivatives

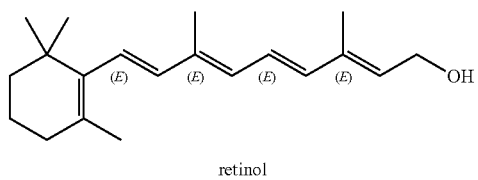

retinol

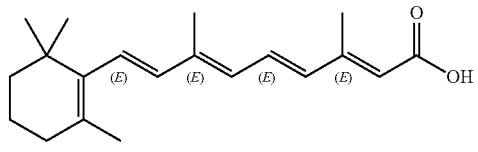

all-trans-retinoic acid

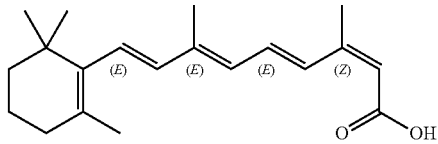

13-cis-retinoic acid

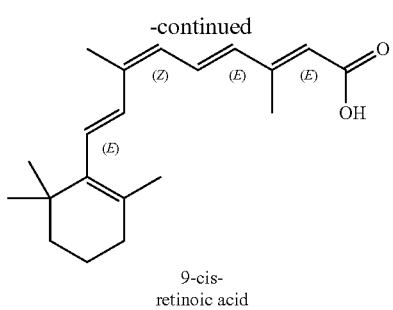

9-cis-retinoic acid

2nd generation of RA and its derivatives

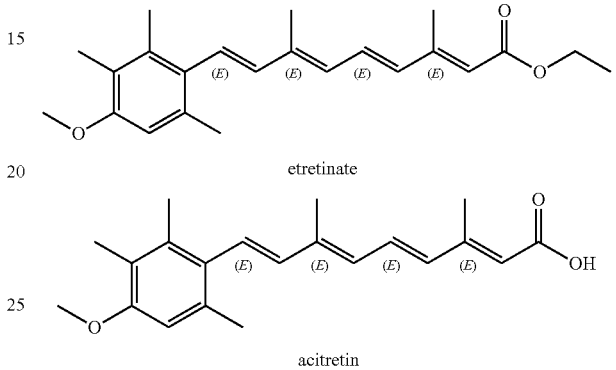

etretinate acitretin

3rd generation of RA and its derivatives

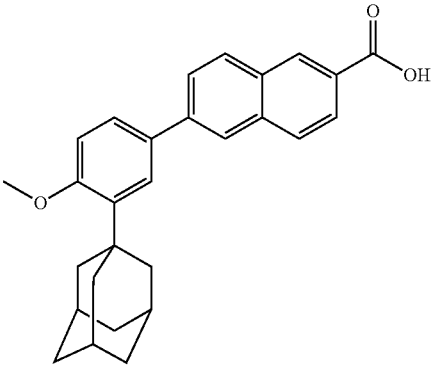

adapalene bexarotene tazarotene

ALDH1A Protein and its Agonist

As used herein, the term "ALDH1A" refers to the Aldehyde dehydrogenase family 1 member A.

In the present invention, ALDH1A includes homologous proteins from various mammals, such as ALDH1A from human and non-human mammals such as rodents (e.g., mice, rats), cows, sheep, dogs, etc. In the present invention, the term includes not only wild-type ALDH1A but also mutant ALDH1A (the mutant ALDH1A has same or similar activity as that of wild-type ALDH1A).

In the present invention, the representative ALDH1A includes, but is not limited to, ALDH1A1, ALDH1A2, ALDH1A3, and combinations thereof.

As used herein, the term "agonist of ALDH1A protein" is a substance that increases the expression and/or activity of ALDH1A. For example, it is a substance that has a high affinity with the ALDH1A protein and can bind to ALDH1A to achieve an effect of enhancing ALDH1A.

In a preferred embodiment of the invention, the agonist of ALDH1A protein is a compound selected from the group consisting of N-(1,3-Benzodioxol-5-ylmethyl)-2,6-dichlorobenzamide (abbreviation is ALDA-1), N-(1,3-Benzodioxol-5-ylmethyl)-2,6-dichlorobenzamide, 2-(benzo[d][1,3]dioxol-5-yl)-N-(5,6-dihydro-4H-cyclopenta[c]isoxazol-3-yl)acetamide, 6-methyl-2-(phenylazo)-3-pyridinol.

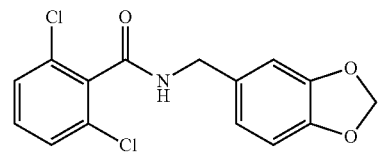

ALDA-1
N-(1,3-Benzodioxol-5-ylmethyl)-
2,6-dichlorobenzamide

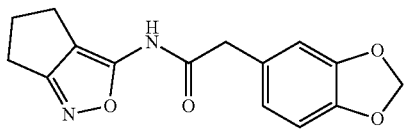

2-(benzo[d][1,3]dioxol-5-yl)-N-(5,6-dihydro-
4H-cyclopenta[c]isoxazol-3-yl)acetamide

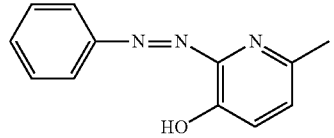

SIB-1757
(6-methyl-2-(phenylazo)-3-pyridinol)

ALDH1A Inhibitor

ALDH1A inhibitor (or inhibitor of ALDH1A family) is a substance that blocks or reduces the rate of chemical reaction of ALDH1A and its family proteins in biochemical reactions. In addition, the term also includes an inhibitor that reduces the expression or activity of ALDH1A, such as antisense RNA, miRNA, or antibody.

In a preferred embodiment of the invention, the inhibitors of ALDH1A and its family are compounds selected from the group consisting of:

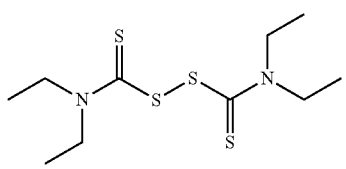

Disulfiram

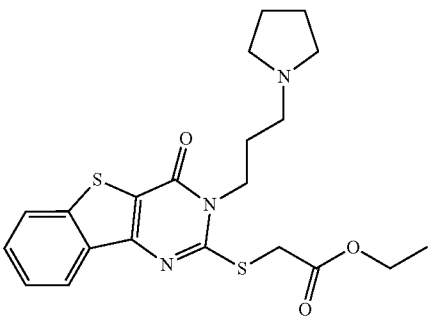

A37 (CM 037)

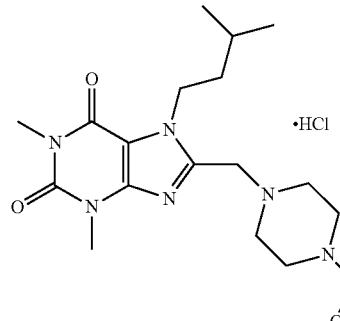

NCT-501 hydrochloride

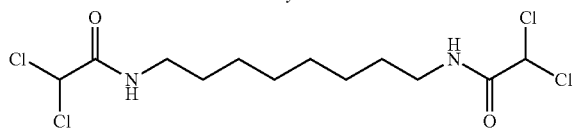

WIN-18446

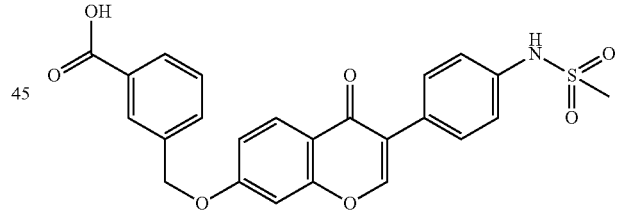

CVT-10216

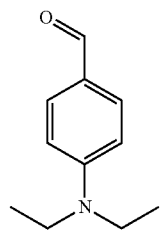

DEAB, 4-(N,N-diethyl)aminobenzaldehyde

Inhibitors of RA Degrading Enzyme CYP26A1

The inhibitor of RA-degrading enzyme CYP26A1 refers to a substance that blocks or reduces the rate of degradation of retinoic acid by the CYP26A1 protein in a biochemical reaction.

In a preferred embodiment of the invention, the inhibitor of RA degrading enzyme CYP26A1 is a compound selected from the group consisting of:

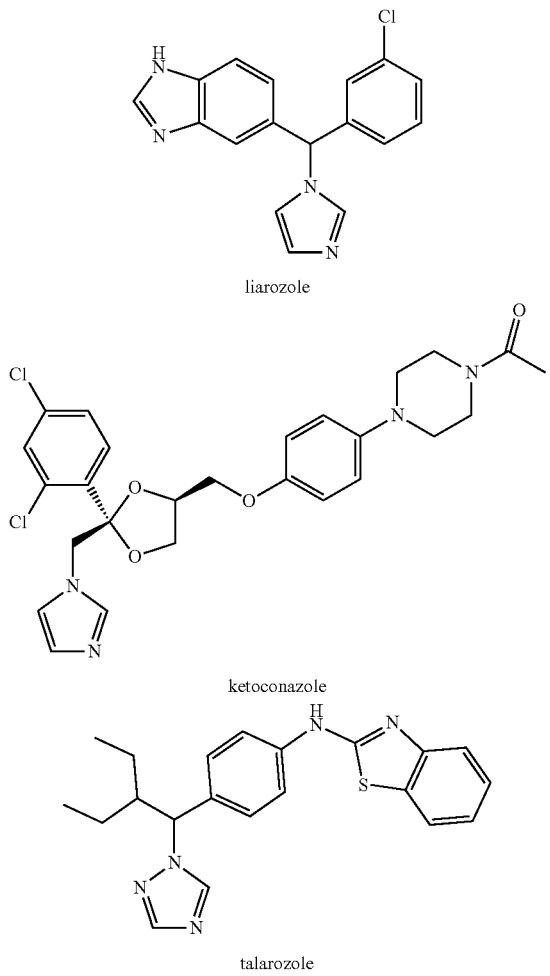

liarozole ketoconazole talarozole

Candidate Drug or Therapeutic Agent

In the present invention, it also provides a method of screening a drug candidate (or a potential therapeutic agent) for treatment or prevention of autism.

In the present invention, a drug candidate or a therapeutic agent refers to a substance which is known to have a certain pharmacological activity or is being tested and which may have a certain pharmacological activity, including but not limited to nucleic acid, protein, chemically synthesized small molecule or large molecular compounds, cells, and so on. The drug candidate or therapeutic agent can be administered orally, intravenously, intraperitoneally, subcutaneously, or via a spinal canal.

The main advantages of the invention include:

(1) The present invention provides a novel therapeutic target for autism. Therefore, it is possible to screen out a drug for treating autism according to the present invention.

(2) The present invention can also be used to screen for the potential risk of autism in the offspring caused by the side effects of administration of medicines and application of daily chemicals by pregnant women (as well as the side effects of administration of medicines and application daily chemicals by infants and young children). It is possible to develop an effective clinical assessment diagnostic tool.

The present invention is further described in combination with specific embodiments. It should be understood that these examples are only for illustrating the present invention and are not intended to limit the scope of the present invention. The experimental methods that do not specify the specific conditions in the following examples are generally performed according to conventional conditions such as those described in Sambrook et al., Molecular Cloning: A Laboratory Manual (New York: Cold Spring Harbor Laboratory Press, 1989), or according to the conditions recommended by the manufacturer. Unless otherwise indicated, percentages and parts are percentages by weight and parts by weight. The experimental materials involved in the present invention are commercially available unless it is otherwise specified.

Materials and Methods

1. Subject and Sample

The recruitment and evaluation of the subjects involved were based on the Constitution of the National Key Laboratory of Medical Genetics, School of Life Sciences, Central South University, and were strictly adhered to the principles of the Helsinki Declaration. Details of subject recruitment and diagnosis were performed as previously reported (Xia et al., 2013; Wang et al., 2016). Written consent forms were received for all blood sample collections.

2. Sequence Analysis of Copy Number Variation (CNV)

The copy number variation (male, aged 3-6 years) of 3 patients of Han nationality was analyzed using the Human660W-Quad microarray chip (Illumina). Chip analysis was performed using GenomeStudio v2011.1 (Illumina) according to previous reports (Nava et al., 2013). The plotting of the copy number variation was performed using the human reference genome hg18 as a reference.

3. Cell Culture and Transfection

Blood cells were transformed with EBV virus according to a standard method (Anderson et al., 1984) to obtain immortalized lymphocytes, and were cultured in RPMI-1640 (Gibco) medium containing 10% fetal bovine serum (Biochrom). HEK-293FT (Life Technologies), HEK-293 (ATCC), SH-SY5Y (ATCC), H1299 (ATCC) and A549 (ATCC) cells were all cultured in DMEM (Corning) medium contain 10% fetal bovine serum and penicillin/streptomycin (Life Technologies). Mouse fibroblasts were prepared and established according to previously reported methods (Xu et al., 2005). Primary neuronal cells were isolated from the prefrontal cortex of fetal rat brain of the 18-day-aged rat (Sprague Dawley) and cultured in DMEM/F12 medium containing 10% fetal bovine serum. The next day, the cell culture medium was changed into serum-free neurobasal medium (Gibco) containing B-27 supplement (Gibco) and GlutaMax (Gibco). The cells were cultured in a incubator under 5% $CO_2$ and saturated humidity. All cell lines were tested for mycoplasma regularly.

HEK-293FT cells were transfected with the corresponding plasmids using polyethylenimine (Sigma), and SH-SY5Y and H1299 were transfected with Lipofectamine 2000 (Life Technologies), wherein the operations were all according to the manufacturer's instructions. The UBE3A single allele knockout and the biallelic knockout cell lines based on H1299 cells were screened out after genome edition by the CRISPR/Cas9 system. The design of sgRNA primer for UBE3A gene followed the previous reports (Hsu et al., 2013), and the sequences were listed below (targeting sequences were underlined):

(1) 5'-CACCG<u>AGCACAAAACTCATTCGTGC</u>-3' (SEQ ID No: 1)

(2) 5'-AAAC<u>GCACGAATGAGTTTTGTGCTC</u>-3' (SEQ ID No: 2)

Primary neuronal cells were transfected with the corresponding plasmids using calcium phosphate transfection reagent (available from Biyuntian) according to the manufacturer's protocol.

4. Construction of Plasmids

The plasmids in this research involved restriction endonuclease digestion and ligation (NEB), which were conducted according to conventional cloning methods. Plasmids for yeast double hybrid screening were obtained using Gateway LR Cloning Enzyme (ThermoFisher) according to the manufacturer's protocol. Point mutations in the relevant plasmids were introduced using site-directed mutagenesis methods. In addition, plasmids containing multiple elements were constructed using the Gibson assembly method. In the experimental work, the fusion expression tags for UBE3A were placed at the N-terminal.

5. Yeast Two-Hybrid

Using UBE3A as a bait protein, pDEST32-UBE3A (ThermoFisher) and a human cDNA library based on the pDEST22 backbone (ThermoFisher) were co-transformed into the yeast strain Mav203 (ThermoFisher). Positive clones were able to survive in a medium lacking uracil, histidine, leucine and tryptophan (Clontech), and also to exhibit blue color in the presence of X-Gal (Sigma).

6. GST Pull Down Experiment

GST, GST-UBE3A and the truncated GST-UBE3A proteins were induced to express in BL21 competent bacterium (NEB) and purified using glutathione agarose (GE Healthcare). ALDH1A1-His6, ALDH1A2-His6 and ALDH1A3-His6 proteins were purified using Ni-NTA agarose (Qiagen). The purified ALDH1A2-His6 and GST-UBE3A proteins were incubated in a pull-down buffer (50 mM Tris-Cl, pH 8.0, 200 mM NaCl, 1 mM EDTA, 1% NP-40, 1 mM DTT, 10 mM $MgCl_2$) at 4° C. for 2 hours. The beads were washed 4 times with the pull-down buffer and analyzed by immunoblotting. The pull-down analysis of other proteins followed the same steps.

7. Reconstruction of Bacterial Ubiquitination System

All components of the ubiquitination system were placed in the vector backbone of pACYCDuet-1 (Novagen) for double expression system using conventional cloning methods. HA-UB, UBCH7 and Uba1 were inserted into the first multiple cloning site, ligated after the T7 promoter/lactose operon and the ribose binding site, and each element was separated by the Shine-Dalgarno (SD) sequence to form a polycistron element. UBE3A was inserted into the second polyclonal cleavage site to generate the pACYC-HA-UB-UBCH7-Uba1-UBE3A plasmid. BL21 competent cells were co-transformed with pACYC and pET22b-ALDH1A2-His6 plasmid (Novagen) via electroporation and screened with chloramphenicol and ampicillin (Sigma). E. coli was induced with 0.25 mM isopropyl-β-D-1-thiogalactoside (IPTG, Sigma) and cultured for 16 hours at 18° C. when the OD600 absorbance reached 0.8. The cells were harvested and resuspended in RIPA buffer (150 mM NaCl, 50 mM Tris-Cl, pH 7.4, 1% NP-40, 0.1% SDS), then the cells were sonicated with a Vibra-Cell processor (SONICS) and the precipitates were removed by centrifugation. The supernatant was purified using Ni-NTA agarose. In the Usp2cc treatment group, the purified proteins bound to Ni-NTA beads were incubated with and Usp2cc enzyme overnight at 4° C. The level of ubiquitination of ALDH1A2 protein was analyzed by immunoblotting.

8. Immunoprecipitation and Immunoblotting Experiments

Cells expressing endogenous or exogenous proteins was lysed in an IP buffer (50 mM Tris-Cl, pH 7.5, 150 mM NaCl, 1 mM EDTA, 1% NP-40, 10% glycerol) supplemented with protease inhibitor cocktail (Roche) and sonicated with a Vibra-Cell processor. After centrifugation, the cell debris was removed, and the supernatant was mixed with a specific antibody and protein G agarose beads (Merck Millipore) and incubated at 4° C. overnight. The primary antibodies used were as follows: normal rabbit IgG antibody (sc-2027, Santa Cruz), Flag antibody (F1804, Sigma), ALDH1A2 antibody (sc-367527, Santa Cruz), HA antibody (H6908, Sigma). After enrichment with immunoprecipitation, 2×SDS-PAGE loading buffer was added and denatured at 95° C. for 10 minutes. The initial protein, the enriched protein via immunoprecipitation and other cell lysate samples were separated by SDS-PAGE gel and transferred onto a PVDF membrane (Bio-Rad). Membranes were immunoblotted with specific antibodies: UBE3A antibody (sc-166689, Santa Cruz, 1:500 dilution), Flag-tag antibody (F1804, Sigma, 1:8000 dilution), HA tag antibody (H6908, Sigma, 1:4000) LDH1A2 antibody (sc-367527, Santa Cruz, 1:500 antibody), ALDH1A1 antibody (15910-1-AP, Proteintech, 1:500 antibody), ALDH1A3 antibody (25167-1-AP, Proteintech, 1:500 dilution), His-tag antibody (H1029, Sigma, 1:4000 dilution), GST-tag antibody (66001-1-1g, Proteintech, 1:5000 dilution), Myc-tag antibody (sc-40, Santa Cruz, 1:1000 dilution), actin antibody (A2228, Sigma, 1:8000 dilution), GAPDH antibody (sc-32233, Santa Cruz, 1:4000 dilution).

9. Immunofluorescence

After transfecting with the specific plasmids, SH-SY5Y cells (ATCC) were cultured for another 24 hours and then fixed with 4% paraformaldehyde (Sigma). After the cells were lysed, primary antibody (Flag-tag antibody, F1804, Sigma) was added and incubated overnight at 4° C., and then incubated with a fluorescent secondary antibody conjugated with Alexa Fluor 488 (A11029, ThermoFisher) for 1 hour at room temperature. The nuclei were counterstained with 4,6-diamidino-2-phenylindole (DAPI, ThermoFisher). Rat primary neuron cells were transfected with the specific plasmids in vitro on day 10 using calcium phosphate transfection, and treated with DMSO (Sigma) or 1 μM tetrodotoxin (TTX, Shanghai Aladdin) and 100 μM D-(−)2-amino-5-phosphate valeric acid (D-APV, Tocris) for 24 hours when it was DIV12. After fixing the cells, the cells were stained by using the primary anti-GluR1 antibody (sc-55509, Santa Cruz), PSD95 antibody (ab18258, Abcam) and the secondary antibody conjugated with Alexa Fluor 488 (A11029, ThermoFisher), Alexa Fluor 647 (A21245, ThermoFisher) according to the previous protocol. Images were acquired with an Olympus FV1200 confocal microscope with a resolution of 1024×1024 pixels. The confocal setting parameters were consistent in the same experiment. The analysis and quantification of fluorescence intensity was preformed by using Image-Pro plus (Media Cybernetics) software.

10. Immunohistochemistry

The brains taken from the mice site-injected with the virus were fixed overnight with PBS containing 4% paraformaldehyde at 4° C., and then immersed in PBS containing 30% sucrose (Sigma). Coronal sections of the brain with 40 μM thickness were cut using a Leica CM3050 S ice cutter (Leica Biosystems) and sections were treated with PBST (0.3% Triton X-100) for 15 minutes at room temperature. Brain sections were then blocked with 3% normal goat serum (Boster) and incubated with Flag-tag antibody (14793, Cell Signaling, 1:800 dilution) overnight at 4° C. Sections were incubated with Cy3-conjugated secondary antibody (111-165-045, Jackson ImmunoResearch) for 1 hour at room temperature, and the nuclei were counterstained with DAPI and sealed with a sealing agent Mowiol (Sigma). Fluorescent images were acquired using an Olympus FV1200 confocal microscope.

11. ALDH1A Enzyme Activity Test

The exogenously expressed ALDH1A2-Flag protein in a HEK-293FT cell transfected or untransfected with UBE3A was enriched using a Flag-conjugated agarose column (Sigma), and then eluted with Flag short peptide formulated in an assay buffer for ALDH1A enzyme activity (0.1 M sodium pyrophosphate, pH 8.0, 1.0 mM EDTA, 2.0 mM DTT). In the study of ALDH1A2 enzyme activity to remove ubiquitination, USP2cc enzyme or bovine serum albumin (BSA) was used to incubate with the eluted protein at 4° C. overnight. The enzyme reaction system consisted of 2.5 mM NAD+, 20 mM DTT and 100 µM propionaldehyde (Sigma) dissolved in the detection buffer for enzyme activity. The dehydrogenase activity was detected on a BioTek Synergy Neo spectrophotometer at 340 nm wavelength at room temperature, measured every 3 minutes. The reaction was terminated when the absorbance of all samples reached the plateau. NADH was used as a standard, and the ALDH1A2 dehydrogenase activity was calculated as follows: (production of NADH (nmol) in total reaction time×dilution of sample)/(reaction time×reaction volume). When measuring the substrate of all-trans retinal (Sigma), an assay kit for acetaldehyde dehydrogenase activity (Cayman) was required. The detection analysis was based on a method of fluorescence quantification. Briefly, in the presence of 100 µM all-trans retinal, the detection of enzyme activity was conducted by detecting the parameters of the fluorophore at the absorption wavelength of 530-540 nm and at the emission wavelength of 585-595 nm so as to minimize the interference of retinal on the absorbance.

12. Aldefluor Detection

Aldefluor detection was performed using the Aldefluor kit (STEMCELL Technologies) according to the manufacturer's steps. Briefly, 1×10$^6$ immortalized lymphocytes and the fluorescent substrate BODIPY-aminoacetaldehyde-diethyl acetate (BAAA-DA) (1.5 µM) were incubated at 37° C. for 30 minutes. Each portion of cells was divided into two aliquots: one for fluorescence analysis and the other for pretreatment with the ALDH inhibitor diethylamine-benzaldehyde (DEAB) provided in the kit as a negative control in flow cytometry.

13. RARE-Luciferase Activity Assay

The construction of the pGL4.22-RARE-TK-luciferase plasmid comprised: cloning 3× RARE (RA-responsive element) into the pGL4.22 vector (Promega). The RA sensor cell line construction method involved transfecting the pGL4.22-RARE-TK-luciferase plasmid into H1299 cells, followed by screening out stable cell lines with puromycin (1 µg/mL, Sigma). The RA sensor cells and the immortalized lymphocytes as the RA donor were co-cultured in a VP-SFM (virus production serum-free medium, Gibco) medium at a ratio of cell number of 1:1. After 8 hours of treatment with 1 µM all-trans retinal (Sigma), the luciferase activity of the cultured cells was examined.

14. Electrophysiological Experiment

Primary neuron cells and the neuronal cells transfected and in vitro cultured 12-14 hrs were treated with 1 µM TTX (Aladdin) and 100 µM D-APV (Tocris) for 24 hours, and patch clamp data were recorded at room temperature. The patch clamp internal solution comprised (unit: mM): 20 KCl, 5 MgCl2, 20 HEPES, 110 K-gluconate, 0.6 EGTA, 2 Na2-ATP, 0.2 Na3-GTP, pH 7.3, 290 mOsm, and internal liquid had an electric resistance of approximately 3-6 MΩ. The cultured cells were placed in an external solution in which the external liquid components comprises (unit: mM): 129 NaCl, 5 KCl, 1 MgCl$_2$, 25 HEPES, 2 CaCl$_2$, 30 glucose, pH 7.3, 310 mOsm. The extracellular fluid also contained 1 µM TTX and 100 µM picrotoxin (Tocris), and mEPSC was recorded at a voltage of −70 mV. The results were analyzed using Mini Analysis software (Synaptosoft).

15. Quantitative RT-PCR

Primary neuron cells were treated with the indicated compounds (1 µM TTX and 100 µM D-APV for 24 hours, or 0.5 µM ATRA for 8 hours), and total RNA was extracted using the RNAsimple total RNA kit (Tiangen). A cDNA sample was obtained via reverse transcription using ReverTra Ace qPCR RT Master Mix (Toyobo). qRT-PCR detection was performed on a CFX96 real-time PCR instrument (Bio-Rad) using SYBR Green Master Mix (Toyobo). The relative amount of transcription of the specific gene was corrected by the ΔΔCt method using Gapdh as an internal reference. The QPCR primer sequences in this experiment were as follows.

```
Gapdh
                                      (SEQ ID No: 3)
5'AGGTCGGTGTGAACGGATTTG3', (SEQ ID No: 4)
5'GGGGTCGTTGATGGCAACA3', GluR1
                                      (SEQ ID No: 5)
5'AACCACCGAGGAAGGATACC3', (SEQ ID No: 6)
5'CGTTGAGGCGTTCTGATTCA3', GluR2
                                      (SEQ ID No: 7)
5'TTCTCCTGTTTTATGGGGACTGA3', (SEQ ID No: 8)
5'CCCTACCCGAAATGCACTGT3'.
```

16. Biotin-Labeled Cell Membrane Surface Protein Analysis

Analysis of biotin-labeled protein on membrane surface was performed following previously reported methods (Aoto et al., 2008). Briefly, after 24 hours of treatment in DMSO or 1 µM TTX and 100 µM D-APV, primary PFC neurons were washed with PBS and then incubated with biotin solution (1 mg/ml EZ-Link Sulfo-NHS-SS-Biotin, Pierce) for 2 hours at 4° C. The reaction was stopped by adding 0.1 M glycine, then the cells were washed 3 times with PBS. Biotin-labeled cells were lysed in cell lysate (PBS containing 25 mM MgCl$_2$, 1% NP-40, 1% Triton X-100, 10% glycerol and protease inhibitors). After centrifugation to remove cell debris, the supernatant and UltraLink Streptavidin resin (Pierce) were incubated overnight at 4° C. Biotinylated proteins were collected by centrifugation and washed 3 times with cell lysis buffer. Proteins were denatured in 2×SDS-PAGE loading buffer at 75° C. for 30 min and immunoblotted with GluR1 antibody (13185, Cell Signaling, 1:500 dilution) and GluR2 antibody (13607, Cell Signaling, 1:500 dilution) in the analysis.

17. Animal Breeding

Mice were housed in 3-5 animals per cage in a standard 12-hour light/12-hour dark cycle with autonomous diet and drinking water. All behavioral experiments were performed under 12 hours of light. All zoological studies were carried out strictly according to the regulations of the Animal Care and Use Committee (IACUC) of the Institute of Biochemical Cell Research of the Chinese Academy of Sciences. The mice in all experiments were male mice with C57BL/6 background (SLAC, China).

18. Virus Preparation and Brain Localization Injection

All designated genes were driven by the Synapsin I (SynI) promoter and the Flag tag was fused at the N-terminal. The coat protein serotype of adeno-associated virus (AAV) was AAV2/9, which was packaged by Shanghai Woyuan Biotechnology Co., Ltd. (Obio). The titers of AAV-SynI-Flag-UBE3A and AAV-SynI-Flag-UBE3A-T508E virus were approximately $1.5 \times 10^{13}$ copies/mL, and the titer of AAV-SynI-Flag-EGFP virus was approximately $9.5 \times 10^{12}$ copies/mL.

Three-week-aged mice were anesthetized with intraperitoneal injection of pentobarbital (50 mg/kg) and fixed on a locator (Rivend, China). 1 µL of PBS-diluted AAV virus was injected at a rate of 0.2 µL/min on both sides of the PFC region in the mouse brain using a syringe pump (Stoelting). The position of the site injection (relative to the front fontanel): AP, +2 mm; ML, ±0.5 mm; DV, -1.3 mm. The amount of virus injected per injection site was: AAV-SynI-Flag-UBE3A and its mutant T508E, $3 \times 10^9$; and AAV-SynI-Flag-EGFP, $1.5 \times 10^9$. The needle was held in place for another 3 minutes to prevent virus reflux. The mice were placed on a 37° C. electric blanket until they recovered completely from the anesthesia. 1-2 days after surgery, mice were intraperitoneally injected with 0.5 mg/ml meloxicam (Sigma, 2 mg/kg) to help the mice to relieve pain. Four weeks after surgery, mice were tested for behavior. In the ATRA compensation experiment, one week after the injection of AAV-SynI-Flag-UBE3A virus, mice were orally administered with ATRA (Sigma, dissolved in olive oil, 3 mg/kg) or olive oil for five consecutive days. Behavioral testing was performed 4 weeks after administration.

19. Disulfiram (DSF) Administration

Four-week-aged mice were given a low dose (0.1 mg/g) or a high dose (0.3 mg/g) of DSF (Sigma, dissolved in olive oil) every two days for 6 weeks. The control group was only given the solvent olive oil (Aladdin). The body weight of the mice was weighed weekly. After 6 weeks of gastric administration, the test of mouse behavior was started. The brains of the control and DSF mice were dissected and taken. After freezing with liquid nitrogen, the brain tissue was homogenized, and ATRA was quantified by the HPLC-MS/MS method as described hereinafter.

20. Experiment of HPLC-MS/MS Quantitative Detection of RA

Sample preparation, retinoid extraction and subsequent HPLC-MS/MS analysis were performed according to the previously reported procedures (Kane et al., 2010). The frozen brains of mice were homogenized on ice with 2 mL of 0.9% saline under red light condition. 13-cis-retinoic acid-d5 (20 ng/mL, TRC) was added into the tissue homogenate as an internal reference. Then, 1.5 mL of 0.025 M potassium hydroxide dissolved in ethanol was added into the homogenate, and after adding 7 mL of n-hexane, the mixture was well-mixed and the aqueous phase was extracted, followed by neutralization with 120 µL of 4 M HCl. Then, the oil phase containing RA and polar retinoids was extracted with 7 mL of n-hexane which was added again. The extract was evaporated under a $N_2$ atmosphere and the dried extract was resuspended with 50 µL of acetonitrile. The samples were analyzed by HPLC on a 2.1×100 mm Supelcosil ABZ+PLUS column (3 urn, Sigma) column. The mobile phases were: A, water containing 0.1% formic acid; B, acetonitrile containing 0.1% formic acid. The instrumentation was an AB Sciex 4000 QTRAP LC-MS/MS system, and the ATRA component was quantified in the APCI cation mode, and the ATRA content in each sample was corrected using a standard ATRA curve.

21. Self-Grooming Experiment

The mice used in the self-grooming experiment were placed in a cage box filled with a filler having a thickness of about 0.5-1 cm for 10 minutes in advance for accommodation. Then, within 10 minutes, the time of self-grooming in mice was recorded by a double-blind experimenter through a stopwatch.

22. Three-Chamber Social Experiment

A three-chamber social experiment was performed according to previously reported procedures (Sztainberg et al., 2015). Briefly, a transparent acrylic box for social experiment was divided into three chambers of uniform size with removable gates mounted on the partition board. An inverted iron mesh cup was placed in each of the left and right chambers. Two days before the experiment, C57BL/6 mice, which were from different family and whose age was matched with the test mice, were placed in two cups as strange mice for 1 hour each day for accommodation. Test mice were randomized into groups and accommodated to the test chamber for 1 hour before the test started. Each test mouse was placed in the center chamber for 10 minutes for self-exploration, and the chamber door was closed. In the first stage, a strange mouse was randomly placed in the left or right cup (avoiding positional bias), and the inanimate article was placed in the cup on the other side. Each test mouse was explored for 10 minutes in the open three-chambers, and the communication time between the test mice and the strange mice or the articles was manually recorded. In the second stage, the test mice were kept in the chamber of the strange mouse for 5 minutes, and then another strange mouse was placed in the cup in which the article was previously placed. The test mice were further explored for 10 minutes, and the communication time between the test mice and the familiar animals or the new animals was manually recorded. The observer did not know the group information of test mice.

23. Testing of Open Field Behavior

Mice were randomized into groups and placed in an open field instrument (Med Associates) for 30 minutes. The Ethovision automatic recording software (Noldus) was used to record the time spent by the mouse in the central region (⅓ to ⅔ of length on each side of the region) and to calculate the ratio of the distance walked in the central region to the total distance.

24. Elevated Cross Maze Experiment

Mice were placed in a closed arm of an elevated cross maze (Med Associates) and recording was started for 5 minutes. Image recording was performed using a camera hanged in the air, and the number of times that the mouse entered into the open arm and the closed arm within 5 minutes was recorded and analyzed using ANY-maze software (Stoelting).

25. Rotating Rod Experiment

After mice were randomized into groups, the motor coordination ability of the mice was recorded using a Rotamex rotarod instrument (Columnbus Instruments). On the same day, the test mice were tested 3 times, each experiment was lasted 5 minutes, and the rotating rod was accelerated from 4 revolutions per second to 40 revolutions per second. There were at least 30 minutes between two experiments. The time before the test mice dropped off the rod was automatically recorded by an infrared detection system, and the results of the last test were finally compared.

26. Statistical Analysis

All data analysis was performed using GraphPad Prism software. Data significance analysis was performed using Student's two-tailed t-test, one-way ANOVA (Bonferroni post-hoc test or Dunnett's post-hoc test), respectively. All data were expressed as mean and variance. The details of each of statistics were given in the legend. All data were collected from a minimum of 3 independent replicates. There was no pre-estimated sample size. All mice were randomly assigned into different groups.

Example 1 Copy Number Amplification of Chromosome 15q11.2-14 was Found in Samples from Autistic Patients In the early stage, three patients with clinically diagnosed autism phenotypes were collected. The genomic DNA extraction and BeadChip chip detection of their peripheral blood revealed an amplification of chromosome 15q11.2-14 (FIG. 1a-b). A series of genes were included in this amplified region, and their association with autism was unclear, except for the UBE3A gene, which was commonly confirmed to play a key role in the 15q amplification syndrome (FIG. 1b-c). Peripheral blood lymphocytes from these patients were constructed into immortalized cell lines using EBV virus infection for subsequent study on functionality. Among them, the expression levels of UBE3A protein were significantly increased in these cells from three autistic patients compared to control cells from healthy volunteers (FIG. 1d).

Example 2 Screening Out the New Substrate ALDH1A Protein Family of UBE3A

Figure 2:
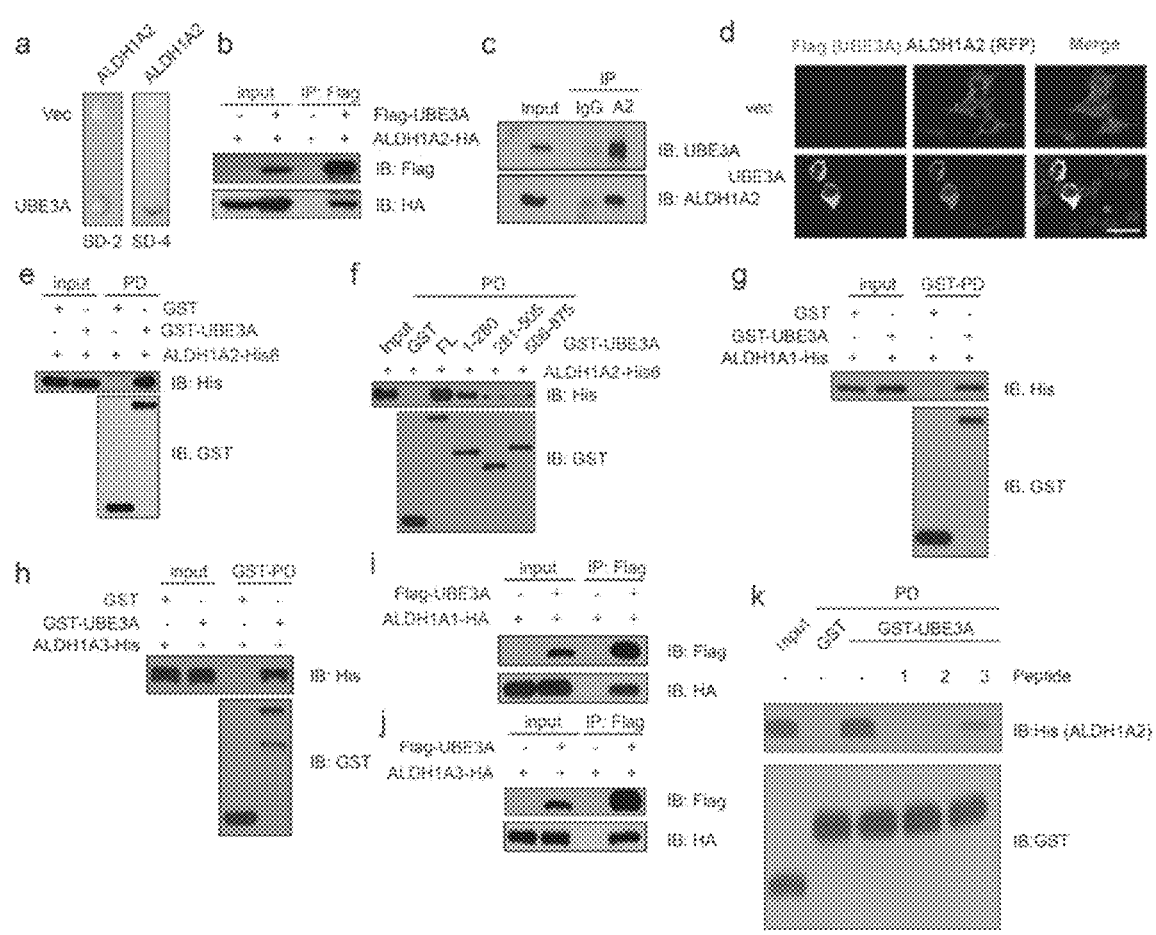
FIG. 2 shows that UBE3A binds to members of the ALDH1A family. (a) Interaction of human UBE3A protein with ALDH1A2 in a yeast two-hybrid assay. Positive clones survive in SD-4 culture plates and appear blue on X-gal. (b-c) There is an interaction between Flag-UBE3A and ALDH1A2-HA or endogenous proteins in 293-FT cells. The tagged proteins expressed in cells were subjected to Co-IP analysis with specific antibodies (b); the endogenous protein Co-IP was carried out with IgG or ALDH1A2 antibody, and immunoblotted with UBE3A or ALDH1A2 antibody (d). (d) Immunofluorescence colocalization experiment was performed on Flag-UBE3A and ALDH1A2-RFP in SH-SY5Y cells, and the nuclei were stained with DAPI. The scale bar represents 30 um. (e) In vitro interaction between UBE3A and ALDH1A2 proteins. (f) Identification of the binding segments of ALDH1A2 and UBE3A. (g-h) UBE3A interacts in vitro with other proteins of the ALDH1A family. (i-j) Human UBE3A interacts in vivo with other members of ALDH1A family. (k) In the GST pull-down experiment, three different peptides (peptide-1, peptide-2, peptide-3) targeting UBE3A-ALDH1A2 binding regions were added, and could competitively block the mutual binding of proteins GST-UBE3A and ALDH1A2 with varying extents.

Since there was no known substrate for UBE3A to explain the association between the onset of ASD and UBE3A overactivation from a mechanical perspective (Glessner et al., 2009), human UBE3A protein was firstly used as a bait to screen for unknown substrate proteins by yeast two-hybrid method. It was found that many positive clones carried cDNA encoding the rate-limiting enzyme ALDH1A2 gene for RA synthesis (FIG. 2a). Retinoic acid or RA, as an active metabolite of vitamin A (retinol), is required for the development and growth of higher animals including human. The synthesis of RA is accomplished in two steps, including retinol dehydrogenase (RDH10), which catalyzes retinol into retinal, and retinal dehydrogenase (ALDH1A1, ALDH1A 2, and ALDH1A 3 families which catalyze retinal into retinoic acid). Endogenous or exogenously expressed UBE3A and ALDH1A2 proteins were confirmed to form complexes in HEK-293FT cells by immunoprecipitation experiments (FIG. 2b-c). In immunofluorescence experiments, Flag-tagged and RFP-tagged UBE3A and ALDH1A2 proteins were co-localized in the cytoplasm of glioma cell SH-SY5Y (FIG. 2d). The GST pull-down experiment further confirmed that the recombinant proteins UBE3A and ALDH1A2 could bind directly in vitro (FIG. 2e) and bound through the N-terminal (amino acid position of 1-280) of UBE3A (FIG. 2f). Since the ALDH1A2 protein had high sequence homology to other family members of ALDH1A1 and ALDH1A 3, it was further verified that UBE3A could bind directly to ALDH1A1 and ALDH1A3, respectively, in vitro and in vivo (FIG. 2g-j). In the GST pull-down experiment, three different peptides (peptide-1, peptide-2, peptide-3) targeting UBE3A and ALDH1A2 binding regions were added. They could block the bonding between GST-UBE3A and ALDH1A2 proteins in different extend (FIG. 2k). The sequences of peptide-1, peptide-2, peptide-3 were as follows:

```
                                         (SEQ ID No: 9)
peptide-1: ASRMKRAAAKHLIERYYHQLTEGCG (SEQ ID No: 10)
peptide-2: NNAAAIKALELYKINAKLCDPH (SEQ ID No: 11)
peptide-3: AEALVQSFRKVKQHTKEELKSLQAKDEDKD.
```

Example 3 UBE3A Ubiquitination of ALDH1A2

Figure 3:
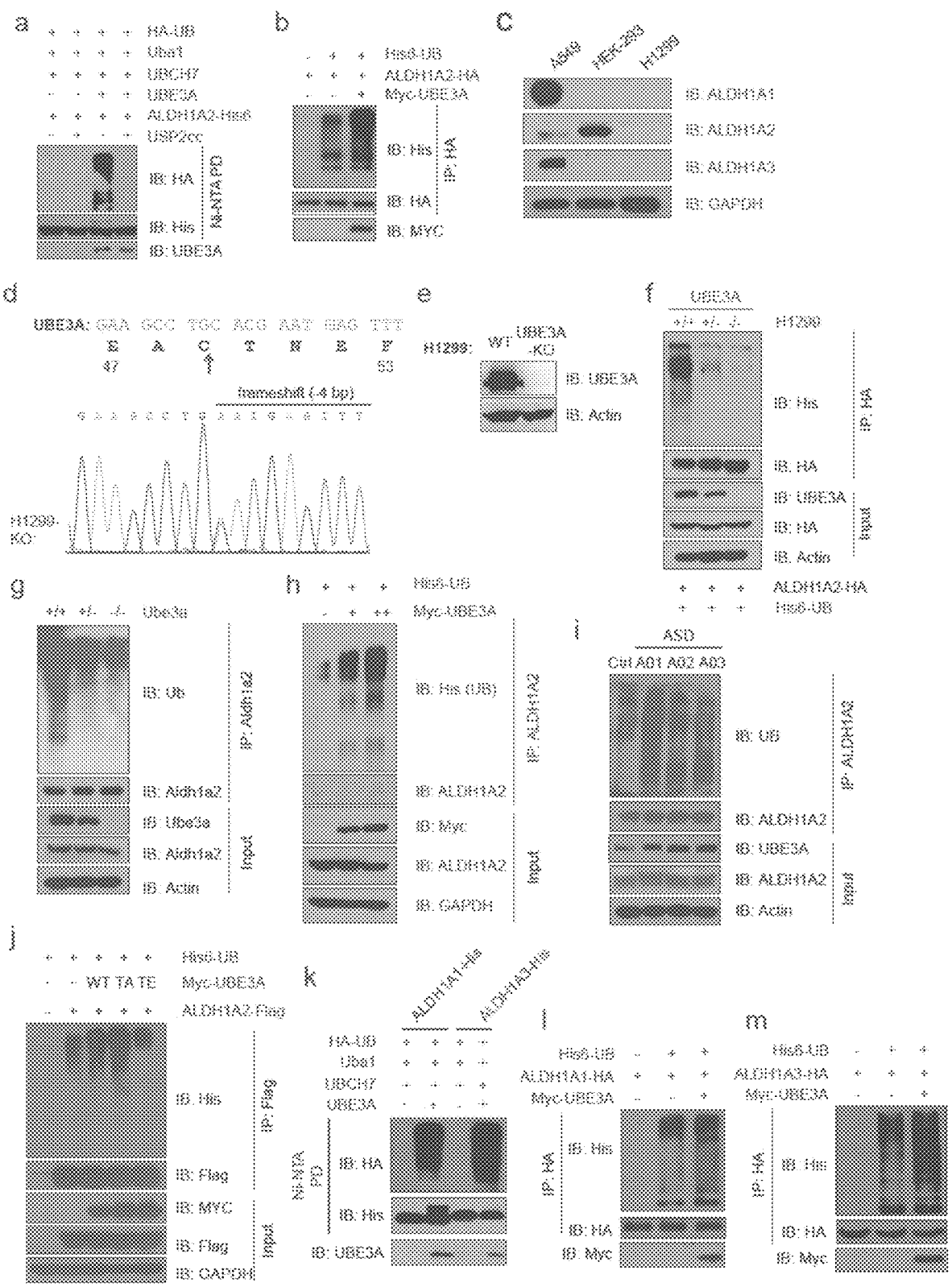
FIG. 3 shows that UBE3A links a polyubiquitin chain to ALDH1A2 in a recombinant ubiquitination system. (a) UBE3A links the polyubiquitin chain to ALDH1A2 in a recombinant ubiquitination system. (b) UBE3A promotes in vitro ubiquitination of ALDH1A2. The ubiquitinated protein was enriched with HA antibody and immunoblotted with anti-His antibody. (c) Detection of the static content of endogenous ALDH1A1, ALDH1A2, and ALDH1A3 proteins in different cell lines. (d) CRISPR targets the UBE3A gene sequence in H1299 cells. Upper part: gene sequence after UBE3A knockout, lower part: sequencing diagram of peak for UBE3A−/− cell. The red arrow indicates the start of the frameshift (4 bp are deleted). (e) IB analysis confirmed that UEB3A gene was knocked out in H1299 UBE3A−/− cells as compared to wild-type H1299 cells. (f) In H1299 cells with different UBE3A (+/+, +/−, and −/−) genotypes, ALDH1A2 ubiquitination decreases as UBE3A is deleted. (g-h) In MEF cells or HEK-293FT cells, the level of endogenous Aldh1a2 ubiquitination was positively correlated with Ube3a protein levels. (i) In lymphocytes from ASD patients, the level of ubiquitination of the endogenous ALDH1A2 protein increases as the UBE3A protein level increases. (j) The phosphorylation status of UBE3A affects its E3 ligase activity on ALDH1A2. (k) UBE3A ubiquitinates other members of the ALDH1A family in the recombinant ubiquitination system. (l-m) UBE3A protein ubiquitinates in vivo other members of the ALDH1A family.

Next, we continued to verify that UBE3A was capable of ubiquitinating ALDH1A2. Firstly, an ubiquitination system was established in $E.\ coli$ (see the method section for details) (Keren-Kaplan et al., 2012). The members required for ALDH1A2 and ubiquitination reactions were co-transformed into bacteria, and IPTG was used to induce protein expression. As shown in FIG. 3a, the ALDH1A2 protein was highly ubiquitinated in the presence of UBE3A protein, and the ubiquitinated band was removed by the de-ubiquitination enzyme USP2 catalytic core USP2cc protein, suggesting that ALDH1A2 was covalently modified via ubiquitin by UBE3A. In HEK-293FT cells, overexpression of UBE3A protein also promoted ubiquitination of ALDH1A2 (FIG. 3b).

In a further study of ALDH1A2, in order to remove interference from endogenous proteins, the expression of ALDH1A family proteins in various cell lines was screened and examined. As a result, it was found that the endogenous expression of the ALDH1A family protein was almost completely undetectable in the H1299 cell line (FIG. 3c). Using the Crispr/Cas9 method, the UBE3A gene in H1299 cells was knocked out, and a significant decrease in the ubiquitination level of the ALDH1A2 protein was observed (FIG. 3d-f). Similarly, in the MEF cells from UBE3a knockout mice, the level of ubiquitination of the Aldh1a2 protein was correspondingly reduced as the Ube3a protein was reduced as compared to MEF cells in the control normal group (FIG. 3g). Since ALDH1A2 protein still had some degree of modification of ubiquitination in human UBE3A−/− and mouse Ube3a−/− cells, there might be other unknown E3 ubiquitin ligase capable of ubiquitinating the modified ALDH1A2 protein. Summing up, these results clearly demonstrated that the proteins of ALDH1A family, including ALDH1A2, were substrates for the E3 ubiquitin ligase UBE3A.

Since the overactivation of UBE3A was closely related to autism, we attempted to further validate that the high activity of UBE3A could increase the ubiquitination of ALDH1A2 in vivo. In HEK-293FT cells, the level of ubiquitination of ALDH1A2 showed a significant increase dependent on the dose of UBE3A (FIG. 3h). Moreover, the level of endogenous ALDH1A2 protein ubiquitination in immortalized autism lymphocyte strains was significantly higher than that in the normal control group (FIG. 3i), suggesting that the high-dose UBE3A protein associated with autism did indeed catalyze high level of ALDH1A2 ubiquitination.

In a previous study, the Urease 508 site (T508) of UBE3A has been reported to be phosphorylated by protein kinase A (PKA) so that its ubiquitin ligase activity is inhibited. However, it has been found that in autism cases, the ubiquitin ligase activity appears to be over-activated due to the incapability of phosphorylation in T508A mutant (Yi et al., 2015). At the same time, the UBE3A phosphorylation mimetic mutant T508E was found to completely lose E3 ubiquitin ligase activity and was therefore used herein as a ligase mutant without activity. By detecting the Flag-ALDH1A2 protein enriched from HEK-293FT cells, overexpression of UBE3A protein could significantly increase ubiquitination of ALDH1A2, and T508A mutants increased more significantly. However, overexpression of T508E mutant would not increase the ubiquitination level of ALDH1A2 at all (FIG. 3j). These results demonstrated that UBE3A$_{T508E}$ did completely lose E3 ubiquitin ligase activity at least in the aspect of catalyzing ALDH1A2 ubiquitination. In summary, it was found in several tested cell lines that the level of ubiquitination of ALDH1A2 was closely related to the level of UBE3A protein.

Considering the high homology of the proteins in ALDH1A family and the direct association between each of the members mentioned hereinabove and UBE3A, it was further verified whether UBE3A could ubiquitinate and modify ALDH1A1 and ALDH1A3. It was found that both ALDH1A1 and ALDH1A 3 could be ubiquitinated by UBE3A in both prokaryotic and mammalian cells (FIG. 3k-m).

Therefore, UBE3A was capable of ubiquitinating the unique retinal dehydrogenase family ALDH1A of the RA synthesis family. Therefore, it was also concluded that UBE3A could affect the anabolism of RA in cells.

Example 4 UBE3A Modifies ALDH1A2 with Non-Proteasome-Dependent Ubiquitination

Figure 4:
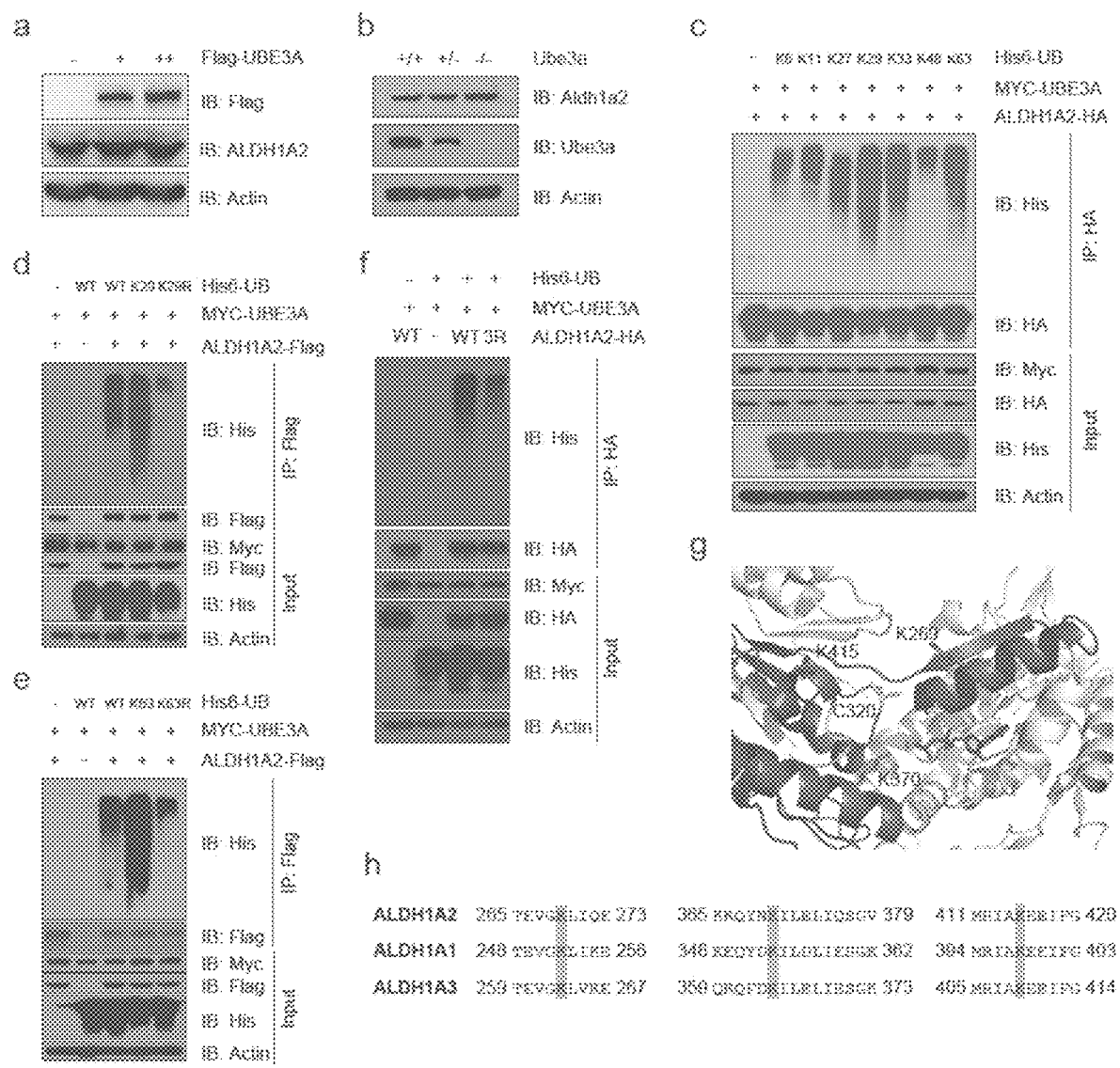
FIG. 4 shows that human UBE3A ubiquitinates ALDH1A2 by non-protein degraded Ub linkage. (a-b) The levels of endogenous ALDH1A2 protein in HEK-293FT cells with overexpressed exogenous Flag-UBE3A protein or in MEF cells with Ube3a of wild-type, deletion or knockout (Ube3a+/+, +/−, −/−). (c-e) UBE3A regulates ubiquitination of ALDH1A2 by K29 and K63 polyubiquitin linkages. Myc-UBE3A, ALDH1A2-HA (or ALDH1A2-Flag), and His-Ub mutant (c) with only one Lys at a specific position, or mutant in which only K at K29 (d) or 63 (e) is mutated into R were co-transformed into H1299 cells. The ALDH1A2 proteins tagged with HA or Flag were enriched in cells and detected with anti-HA or anti-Flag antibodies. (f) His6-Ub, Myc-UBE3A, and HA-ALDH1A2 containing the K->R at the specified positions were co-transformed into H1299 cells. ALDH1A2-HA was enriched with anti-HA antibody and detected for ubiquitination. 3R: the Ks in ALDH1A2-HA were mutated into R at K269, K370, and K515. (g) The crystal structure of the human ALDH1A2 protein monomer, wherein three major ubiquitination sites (marked in red) are located near the active center (Cys320, highlighted in yellow) and the coenzyme NAD+ is marked in purple. The crystal structure was extracted from the PDB database (DOI: 10.2210/pdb4x2q/pdb). (h) Sequence alignment of peptides in the vicinity of ubiquitination site of proteins of the human ALDH1A family, wherein the ubiquitination site is marked in orange.

In the previous report, in the absence of the human papillomavirus oncogene E6, some UBE3A substrate proteins such as HHR23A (Kumar et al., 1999) and RING1B (Zaaroor-Regev et al., 2010) could be ubiquitinated and proteasome-dependently degradated. However, when p53 is deleted in E6, UBE3A alone could not ubiquitinate and further degrade the proteins (Ansari et al., 2012). However, in HEK-293FT cells, there was no change in the expression level of endogenous ALDH1A2 as the expression level of UBE3A protein increased (FIG. 4a). Meanwhile, the expression level of Aldh1a2 protein was also unchanged in mouse MEF cells containing different Ube3a protein levels (FIG. 4b). The ALDH1A2 protein levels were also consistent in immortalized lymphocyte lines, including those cells from autistic patient sources and from healthy volunteer (FIG. 3i). These results suggested that ubiquitination of ALDH1A2 by UBE3A did not promote substrate degradation as observed in other substrates.

Since ubiquitin included seven lysine (Lys) residues, each lysine residue along with the alpha-amino group on the N-terminal methionine, might become a site for covalen binding by ubiquitin molecule during the process of forming an ubiquitin chain, thereby ultimately forming a polyubiquitinated chain (poly-Ub) containing different lysine linkages. A method that lysine at a specific position on the ubiquitin protein was retained and all other lysines were mutated into arginine (K-to-R) was used to identify specific binding forms of the polyubiquitinated chain. In FIG. 4c, the forms of polyubiquitinated strand attached to ALDH1A2 protein were mainly via Lys29 and Lys63. Meanwhile, the lysines on K29 and K63 were mutated into arginine, respectively, and the polyubiquitination chain bound to ALDH1A2 was significantly reduced (FIG. 4d-e). These results suggested that ubiquitination modification of ALDH1A2 by UBE3A was mainly based linkage at K29 and K63, and these two ubiquitin chains generally did not lead to proteasome degradation of the catalytic substrate.

Next, the ALDH1A2 protein enriched from bacteria was analyzed by protein mass spectrometry technology to find out the ubiquitination sites of ligation in ALDH1A2 protein which were catalyzed by UBE3A. K269, K370 and K415 were identified as possible catalytic modification sites. In H1299 cells, the ubiquitination levels of the ALDH1A2 mutant protein were significantly reduced when K269, K370 and K415 sites on ALDH1A2 were simultaneously mutated into arginine (FIG. 4f). Further, it was found by protein structure analysis that these three sites were distributed near the active center of the dehydrogenase (FIG. 4g). Further, they were also highly conserved among the three members of ALDH1A (FIG. 4h). Therefore, the UBE3A ubiquitination-modified protein of ALDH1A family mainly occurred near the sites near the dehydrogenase activity center and did not promote degradation of substrate.

Example 5 UBE3A-Mediated Ubiquitination Modification Inhibits Dehydrogenase Activity of ALDH1A2

Figure 5:
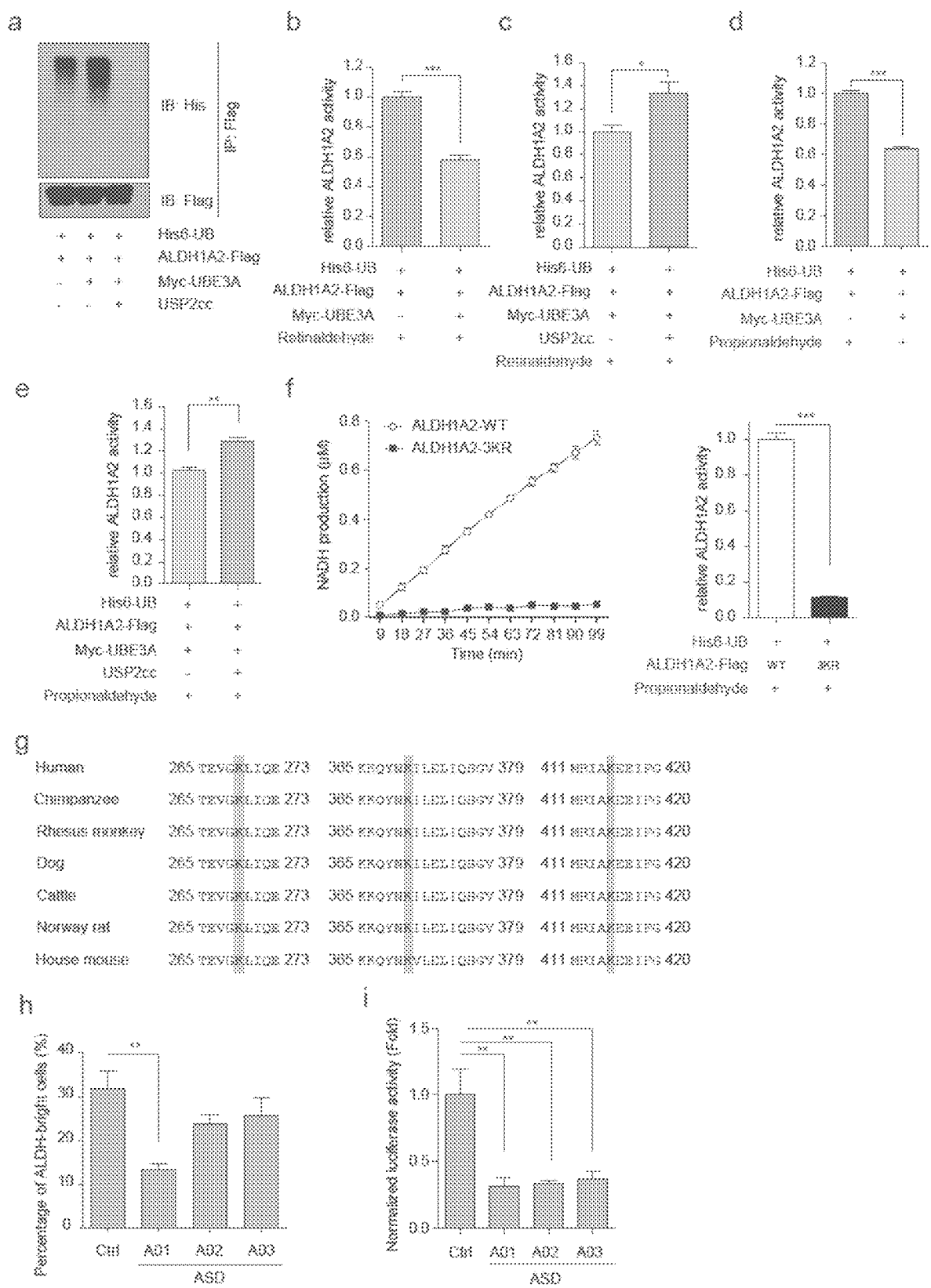
FIG. 5 shows that ubiquitination of UBE3A inhibits activity of ALDH1A2 retinal dehydrogenase. (a) Detection of ALDH1A2-Flag ubiquitination level. The designated plasmids were co-transformed into HEK-293FT cells, and the ALDH1A2-Flag protein was precipitated with anti-Flag antibody, eluted with Flag short peptide, and treated with USP2cc overnight at 4° C. (b-c) The polyubiquitin chain bound on ALDH1A2 by UBE3A reduced the dehydrogenase activity on retinal. The ALDH1A2-Flag protein was enriched from 293FT cells overexpressing Myc-UBE3A, His6-Ub and ALDH1A2-Flag (b), wherein the polyubiquitin chain was removed via USP2cc enzyme treatment or was not removed without treatment (c). The enriched ALDH1A2 protein was analyzed for dehydrogenase activity using all-trans retinal as a substrate. The ubiquitinated ALDH1A2 protease activity was corrected as compared to the control group (b: n=4; c: n=3). (d) Influence of ubiquitination of ALDH1A2-Flag on propionaldehyde dehydrogenase activity was analyzed. *, P<0.001, two-tailed t-test, n=4. (e) ALDH1A2-Flag protein, whether it was treated with USP2cc, was analyzed for propionaldehyde dehydrogenase activity. , P<0.01, two-tailed t-test, n=3. (f) The influence of wild-type ALDH1A2 protein or 3KR protein on propionaldehyde dehydrogenase activity was analyzed. Enzyme activity was expressed as corrected NADH production (left) and relative enzyme activity (right). ***, P<0.0001, two-tailed t-test, n=3. (g) Amino acid sequence alignments near three major ubiquitination sites (K269, K370, and K415) in different species. (h-i) The total ALDH1A activity in immortalized lymphocytes from ASD patients was lower than that in normal control in an AldeFluor analysis (h) or RARE-luciferase analysis (i). The data was presented as mean and variance. *, P<0.05, , P<0.01, *, P<0.001; (b, c) two-tailed t-test, one-way ANOVA Dunnett's post-hoc test (h, i).

Further, it was necessary to detect the dehydrogenase activity of ubiquitinated ALDH1A2 and, in particular, whether it catalyzed the activity of retinal into retinoic acid. As a result, it was found that the retinal dehydrogenase activity of the highly ubiquitinated ALDH1A2 protein enriched from HEK-293FT cells overexpressing UBE3A protein was reduced by half as compared with cell sample in control. However, after the protein was treated with de-ubiquitinating enzyme USP2cc in vitro, there was a significant recovery in activity (FIG. 5a-c). These results showed that the ALDH1A2 ubiquitination modification by UBE3A did significantly down-regulate the retinal dehydrogenase activity. Similarly, another substrate for ALDH1A2, propionaldehyde, was tested and it was found that the activity of ALDH1A2 propionaldehyde dehydrogenase was also reduced, while the USP2cc protein could reverse this phenomenon (FIG. 5d-e). Moreover, the K269/K370/K415 triple mutant of ALDH1A2 completely lost the dehydrogenase activity (FIG. 5f), suggesting that the integrity of these three lysine residues for ALDH1A2 dehydrogenase activity might be particularly important for hydrogenase activity of the entire ALDH1A protein family (FIG. 5g).

Flow cytometry-based Aldefluor detection methods were very common when cellular ALDH activity was studied (Storms et al., 1999). The working principle thereof was that intracellular ALDH could oxidize BAAA (BODIPY-aminoacetaldehyde) into BAA (BODIPY-aminoacetate), while BAA as a negative charge product would remain in the cell, thus the cell ALDH dehydrogenase activity could be quantified by detecting the fluorescence intensity of cells containing BAA. As shown in FIG. 5h, the proportion of ALDH positive cells in autistic lymphocytes was reduced by approximately 20% to 50% as compared to the normal control lymphocytes. This also suggested that a high dose of UBE3A associated with autism might result in down-regulation of ALDH enzyme activity in cells.

Meanwhile, a co-cultured cell system was established to further verify the ALDH1A dehydrogenase activity in autistic cells. First, the luciferase plasmid carrying the RA response element RARE was introduced into H1299 cells, thereby forming RA-responsive cells; the immortalized lymphocyte strain was used as an RA-producing cell. The two kinds of cells were co-cultured in serum-free medium VP-SFM at a ratio of 1:1. The luciferase activity was detected after 8 hours of treatment with retinal. As shown in FIG. 5i, H1299 luciferase activity in a co-cultured autism lymphocytes was down-regulated by 60% as compared to the normal control lymphocytes.

Summing up, these results suggested that UBE3A overactivation associated with autism could inhibit RA biosynthesis, thereby downregulating overall RA homeostasis levels.

Example 6 UBE3A Overactivation Causes Imbalance in Synaptic Homeostasis

Figure 6:
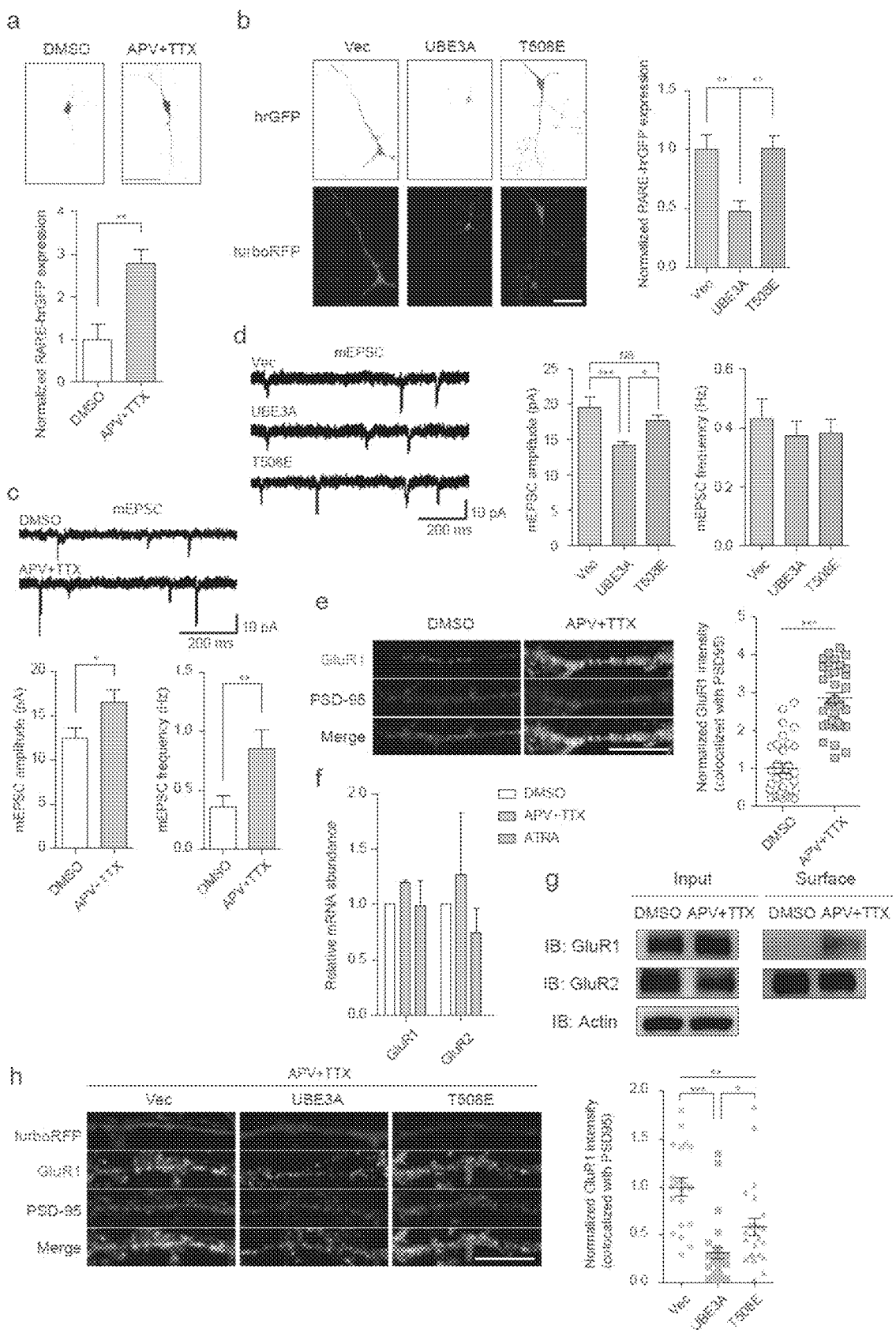
FIG. 6 shows that over-high UBE3A activity disrupts the plasticity of synaptic transmission. (a) REAR-hrGFP brightness was significantly enhanced in primary PFC neurons after neurological activity was blocked with 1 μM and 100 μM TTX. The representative image was in the upper part (bar, 50 um), and the fluorescence intensity was corrected with that in the DMSO group. DMSO, n=8; APV/TTX, n=11. (b) After the primary neurons were treated with 1 μM and 100 μM TTX, introduction of UBE3A significantly reduced the RARE-hrGFP signal as compared to the blank vector or T508E mutant. The representative diagram of relative fluorescence intensity was shown on the right. Vector, n=11; UBE3A, n=14; T508E, n=12. bar: 40 urn. (c) Primary neurons treated with 1 μM and 100 μM TTX showed significant increases in mEPSC amplitude and frequency in electrophysiological experiments. The upper part represented the mEPSC trajectory; the lower part represented the quantification of amplitude and frequency (DMSO, n=15; APV/TTX, n=12). (d) Introduction of UBE3A in neurons reduced the frequency of mEPSC as compared to the blank vector and T508E groups after stimulation with 1 μM APV and 100 μM TTX. (vector, n=15; UBE3A, n=17; T508E, n=18). (e) After treatment with DMSO or APV/TTX for 24 h, GluR1 and PSD-95 on the surface of PFC nerve cells were stained (DMSO, n=31; APV/TTX, n=33). The intensity of GluR1 colocalized with PSD-95 was quantified. (f) Blocking of neural activity did not alter the transcription level of particular genes in primary PFC cells. (g) Blocking neural activity significantly upregulated GluR1 on the membrane surface of primary PFC cell, rather than the protein level of GluR2. (h) After APV/TTX treatment for 24 hours, GluR1 and PSD-95 were stained on the membrane surface of nerve cell after introduction of blank vector, T508E or UBE3A. Quantitative analysis of GluR1 colocalized with PSD-95 in turboRFP positive dendrites (vector, n=21; UBE3A, n=28; T508E, n=24). The data are presented as mean and variance. *, P<0.05, , P<0.01, *, P<0.001; (a, c, e) two-tailed t-test, (b, d, h) one-way ANOVA Bonferroni post-hoc test.

In the adult nervous system, RA has been gradually found to play an important role in homeostasis synaptic plasticity (Chen et al., 2014). In neuron cells, synaptic calcium levels decreased rapidly when synaptic transmission was blocked, and RA was activated by the synthesis of ALDH1A dehydrogenase (Chen et al., 2014; Aoto et al., 2008). RA relieved protein translation process originally blocked by RARα by binding to the RARα protein localized in the synapse, where the regulated protein included AMPA receptor, thereby upregulating synaptic transmission (Aoto et al., 2008). In primary neuron cells from the rat PFC cortex, after inhibiting synaptic activity by D-APV and TTX, RA levels in the cells increased, thereby inducing significant expression of human sea-renal green fluorescent protein (hrGFP) driven by RARE (FIG. 6a). However, after co-transfection of UBE3A-IRES-turboRFP and RARE-hrGFP reporter plasmids into neuron cells, treatment with D-APV and TTX no longer induced hrGFP protein expression (FIG. 6b). However, after co-transfection of mutant T508E with deleted UBE3A ligase activity and RARE-hrGFP reporter plasmid, treatment with D-APV and TTX could induce expression of hrGFP protein to a level similar to that in the control group (FIG. 6b). These results demonstrated that over-activation of UBE3A prevented RA production caused by blockage of synaptic transmission.

Subsequently, it was interesting whether overactivation of UBE3A affected the synaptic homeostasis process regulated by RA when neuronal activity was blocked. First, in primary PFC neuron cells, co-treatment of APV and TTX caused a significant increase in the amplitude and frequency of mEPSC (microexcitatory postsynaptic current) (FIG. 6c). This suggested that in neuron cells, excitatory synapses might achieve a compensatory increase through presynaptic and post-synaptic mechanisms. However, in neuron cells overexpressing UBE3A, the same activity was blocked as compared to the control group, resulting in a decrease in mEPSC amplitude of about 30%. However, in the neuron cells overexpressing $UBE3A_{T508E}$, the increased mEPSC amplitude was similar to that of the control group (FIG. 6d). Also, in cells overexpressing UBE3A and $UBE3A_{T508E}$, the frequency of mEPSC was almost identical to that of the control group (FIG. 6d). Therefore, these results suggested that over-activation of UBE3A was likely to disrupt RA-regulated synaptic homeostasis through post-synaptic mechanisms rather than presynaptic mechanisms when neuronal activity was blocked.

It is now known that postsynaptic mechanisms of synases is mainly to increase the number of excitatory synaptic receptors by promoting translation of synaptic receptors (Han et al., 2009). Consistent with previous reports (Aoto et al., 2008), when neuronal activity was blocked, the protein level of the GluR1 receptor was increased, while the protein level of GluR2 was unchanged; and its transcription level was not affected (FIG. 6e-g). However, in neuron cells expressing UBE3A, blockage of neuronal activity did not increase the protein level of postsynaptic GluR1 (FIG. 6h). In the cells expressing $UBE3A_{T508E}$, the blockage of neuronal activity induced GluR1 protein level to be significantly higher than that in the UBE3A expression group. These results suggested that synaptic homeostasis caused by overactivation of UBE3A was mainly through the process of post-synaptic protein translation that affected up-regulation of RA.

Example 7 Overactivation of UBE3A in Mice Causes Autism Phenotype

Figure 7:
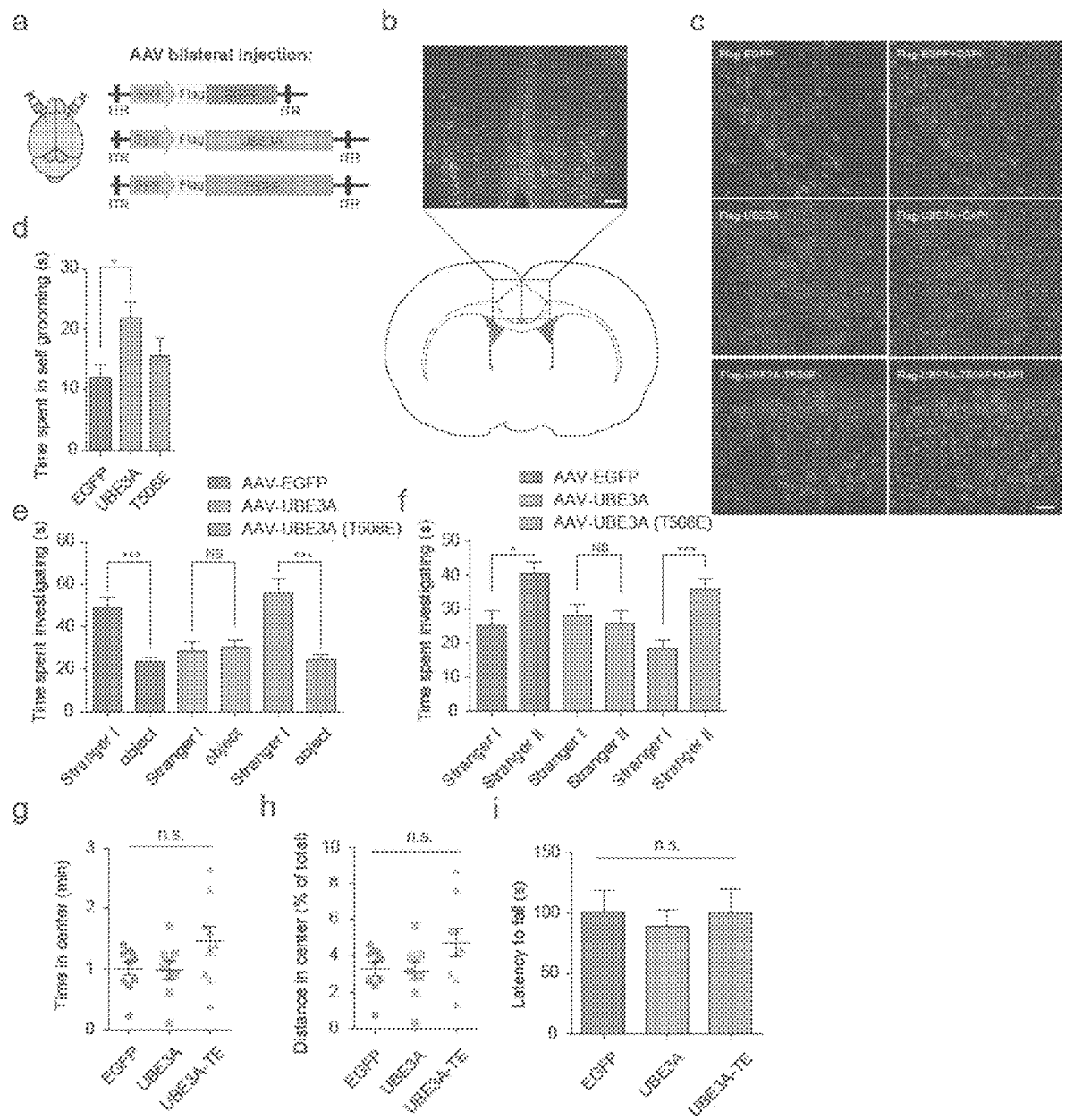
FIG. 7 shows that excess UBE3A protein down-regulates the homeostasis of RA and induces a similar phenotype of ASD in mice. (a) Schematic diagram of the brain for site-directed injection in the PFC region (left), and structural diagram of the expression of Flag-EGFP, Flag-UBE3A or Flag-T508E driven by hSynI-promoter (right). (b) Representative diagram of coronal sections of mice brain injected with AAV-SynI-Flag-EGFP into the PFC region. Bar, 100 um. (c) The Flag-labeled EGFP, UBE3A and T508E proteins were shown in the PFC region. The nuclei were counterstained with DAPI. Bar, 50 urn. (d) The self-grooming time of mice in which AAV virus carrying EGFP, UEB3A, and UBE3A-T508E was site-injected. EGFP (n=11), UBE3A (n=14), UBE3A-T508E (n=9). (e) Comparison of the communication time between the three groups of mice and strange mice or articles. EGFP, n=12; UBE3A, n=13; T508E, n=11. (f) Comparison of the communication time of the three groups of mice with the unfamiliar mouse I and the strange mouse II. EGFP (n=10), UBE3A (n=14), T508E (n=11). *, P<0.05, , P<0.01, *, P<0.001. (g) Time in the central area of the open field for mice injected with AAV virus carrying EGFP, UBE3A or T508E. (h) The ratio of the distance in the central region of the open field to the total distance walked by the mice injected with EGFP, UBE3A or T508E AAV virus. (i) Comparison of the duration of mice injected with different AAV virus before dropping in the rotating rod test.

The PFC region in the brain regulated various executive functions and higher-order cognitive processes in the brain, including decision making, cognitive mobility, social behavior, learning, and social communication. Recently, the anatomical structure of the PFC region and the associated structural abnormalities with other brain regions have been found to be common in the brains of autistic patients, suggesting that dysfunction of PFC is closely related to the etiology of autism (Stoner et Al., 2014; Chow et al., 2012). In order to verify that over-activated UBE3A could induce autism behavior, adeno-associated virus (AAV) packaged with EGFP, UBE3A and T508E, respectively, was injected into the PFC region of the mouse brain by site-directed injection (FIG. 7a-b). Immunofluorescence results of frozen sections of the brain showed that UBE3A and T508E had similar protein expression levels in the PFC region (FIG. 7c).

After four weeks of brain injection, the mice were tested in behavioral experiments. As shown in FIG. 7d, in the experiment of mice self-grooming, mice overexpressing UBE3A spent twice as much time on self-grooming behavior as compared to mice expressing EGFP; whereas mice expressing T508E spent only 30% more time. This suggested that mice overexpressing UBE3A exhibited repetitive stereotypic behavior. Next, three-chamber social behavioral experiment was used to record and compare the time of communication between mice and social animals or non-social articles. In mice expressing EGFP and T508E, the time spent interacting with social mice (50 seconds) was approximately double of the time in interaction with the articles (23 seconds). However, in mice expressing UBE3A, the time to interact with social mice and time to interact with articles were almost same, 30 seconds (FIG. 7e). This suggested that mice overexpressing UBE3A had severe social interaction disorders. Meanwhile, the mice were also recorded for the time of interaction with familiar social mice and unfamiliar social mice, and compared. Among them, in mice expressing EGFP and T508E, they showed greater interest in unfamiliar social mice than familiar social mice, and spent more time interacting with them (increased about 60-100%). However, mice overexpressing UBE3A spent same time on interacting with familiar and unfamiliar social mice (FIG. 7f). This suggested that overexpression of the UBE3A protein inhibited its perception of social novelty in mice. These behavioral experiments also clearly showed that the overexpression of UBE3A protein but not the ubiquitin ligase inactivated mutant T508E in the mouse PFC brain region could significantly induce the emergence of autism phenotype in mice. These included repetitive stereotypes, social barriers, and cognitive deficits in social novelty.

To further investigate potential phenotypic changes caused by expression of UBE3A or T508E proteins, other behavioral experiments were performed on mice. In fact, in open field experiment, mice expressing these three proteins showed the same level of tropism (FIG. 7g-h). Moreover, the results of the rotating rod experiment showed that overexpression of UBE3A did not affect the motor activity of the mice as compared with the control group (FIG. 7i).

Therefore, overexpression of the UBE3A protein in the mouse PFC brain region could specifically trigger the emergence of core symptoms of autism in mice.

Figure 8:
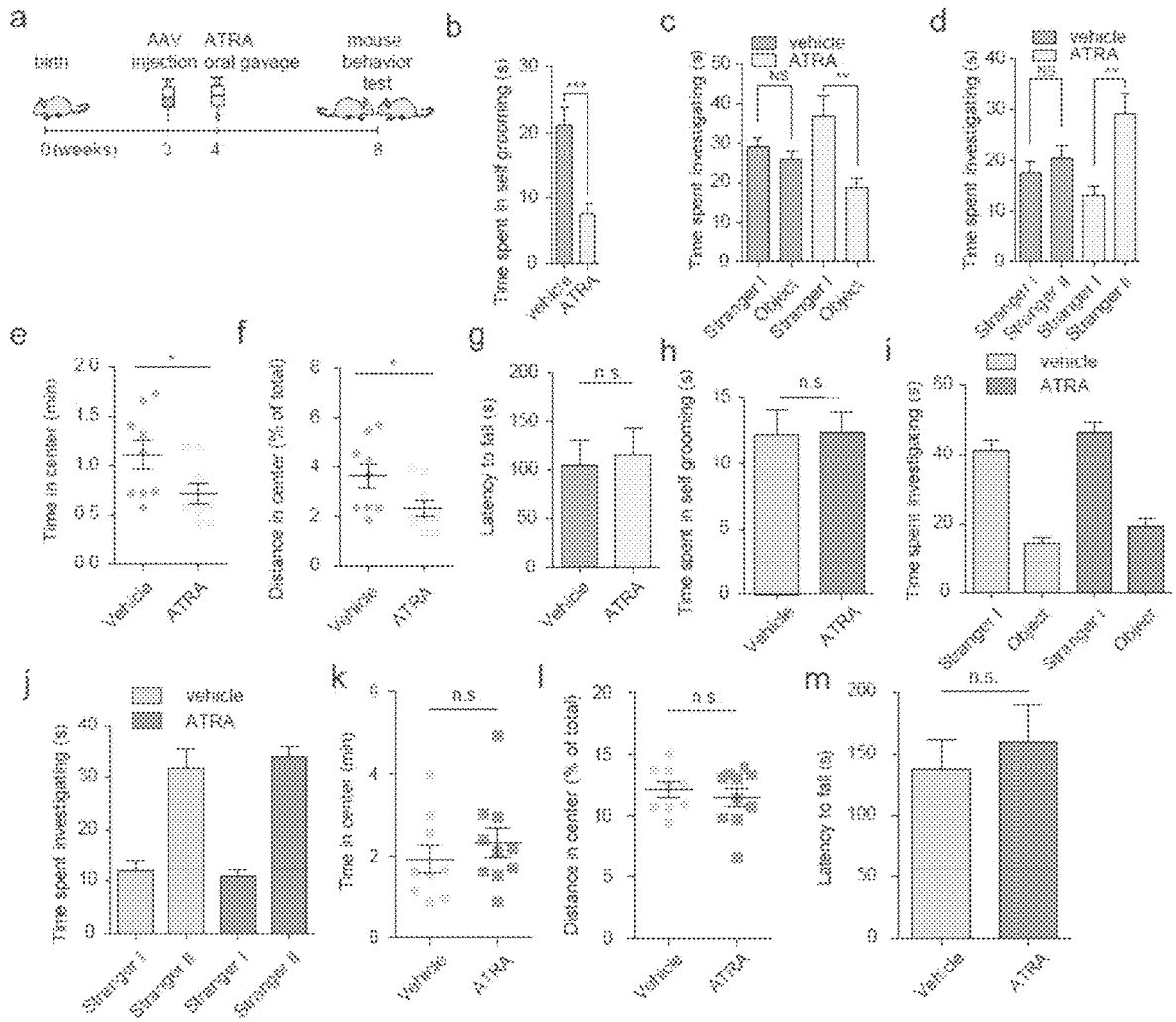
FIG. 8 shows that oral administration of ATRA is able to reverse the autism phenotype occurred in mice overexpressing UBE3A. (a) Schematic diagram of the process of AAV site injection and ATRA replenishment experiment in mice model. (b) After a solvent or ATRA was injected into an AAV-injected mice, the self-grooming time was measured. (olive oil, n=9), ATRA (n=10). (c-d) After injection of solvent or ATRA, the communication time of AAV mice with unfamiliar mouse I and article (c) or with strange mouse I and strange mouse II (d) was compared. (e) Comparison of the residence time in the center of the open field of mice orally administered with a solvent or ATRA. (f) Comparison of the ratio of the distance in the central region of open field to the total distance walked by mice injected with UBE3A AAV virus and orally administered with a solvent or ATRA. (g) Comparison of the duration before dropping in the rotating rod test for mice injected with UBE3A AAV virus and orally administered with a solvent or ATRA. (h) Comparison of self-grooming time in wild-type mice orally administered with a solvent or ATRA. (i-j) Comparison of time of wild type mice orally administered with a solvent or ATRA to explore unfamiliar mouse I and article (i) or strange mouse I and strange mouse II (j). (k-1) Comparison of the residence time (k) in the open field or the walking distance percentage in the central area (1) for wild type mice orally administered with a solvent or ATRA. (m) Comparison of the duration before dropping in the rotating rod test for wild type mice orally administered with a solvent or ATRA. The data was presented as mean and variance.

Example 8 Compensation for RA Attenuates the Autism Phenotype of Mice Caused by Overactivation of UBE3A To further verify whether UBE3A overactivation triggered the autism phenotype in mice due to injury in the RA production process, mice injected with UBE3A-bearing AAV virus in PFC were orally administered with oral solvents (olive oil) or ATRA (3 mg/kg), administered five consecutive days per week for a total of four weeks. Then the mice were subjected to behavioral experiments (FIG. 8a). In the mice self-grooming experiment, the time spent on self-grooming behavior was significantly reduced in mice given oral ATRA as compared to the oral solvent group (FIG. 8b). Meanwhile, the social barriers in ATRA-administered mice were completely reversed as compared with those in the solvent group; and they spent nearly twice as much time on interacting with social animals vs non-social articles (FIG. 8c). As shown in FIG. 8d, the cognitive deficits in social novelty of these mice also appeared to be alleviated after ATRA administration, and the time spent with strange mice were twice as that spent with the familiar mice. Therefore, ATRA administration for four weeks could significantly improve the core symptoms of autism in mice overexpressing UBE3A.

It should be noted that in open field experiment, ATRA-administered mice stayed less time in the middle of the open field and walked more distance than that in the solvent group (FIG. 8e-f), suggesting that ATRA at this dose might cause a certain degree of anxiety in mice overexpressing UBE3A. However, the results of the rotating rod showed that the administration of ATAR did not affect the sport ability of the mice (FIG. 8g).

In order to rule out whether the administration of ATRA would also cause anxiety symptoms in wild-type mice, the same administration and behavioral tests were performed on wild-type mice (FIG. 8a). In fact, the administration of solvent or ATRA did not cause any differences in wild-type mice in self-grooming experiment, three-chamber social interaction experiment, open field experiment, and rotating rod experiment (FIG. 8h-m). These observations indicated that administration of ATRA only produced mild anxiety symptoms in mice overexpressing UBE3A, but has no effect at all on wild-type mice. This also suggested that if ATRA was expected to treat autism later, it is necessary to consider and evaluate its potential side effects.

In conclusion, these ATRA compensation experiments demonstrated for the first time that RA homeostasis played an important role in the development of autism caused by UBE3A overexpression. Meanwhile, the compensation of RA could also be used to alleviate the autism subtype diseases caused by UBE3A overactivation.

Figure 9:
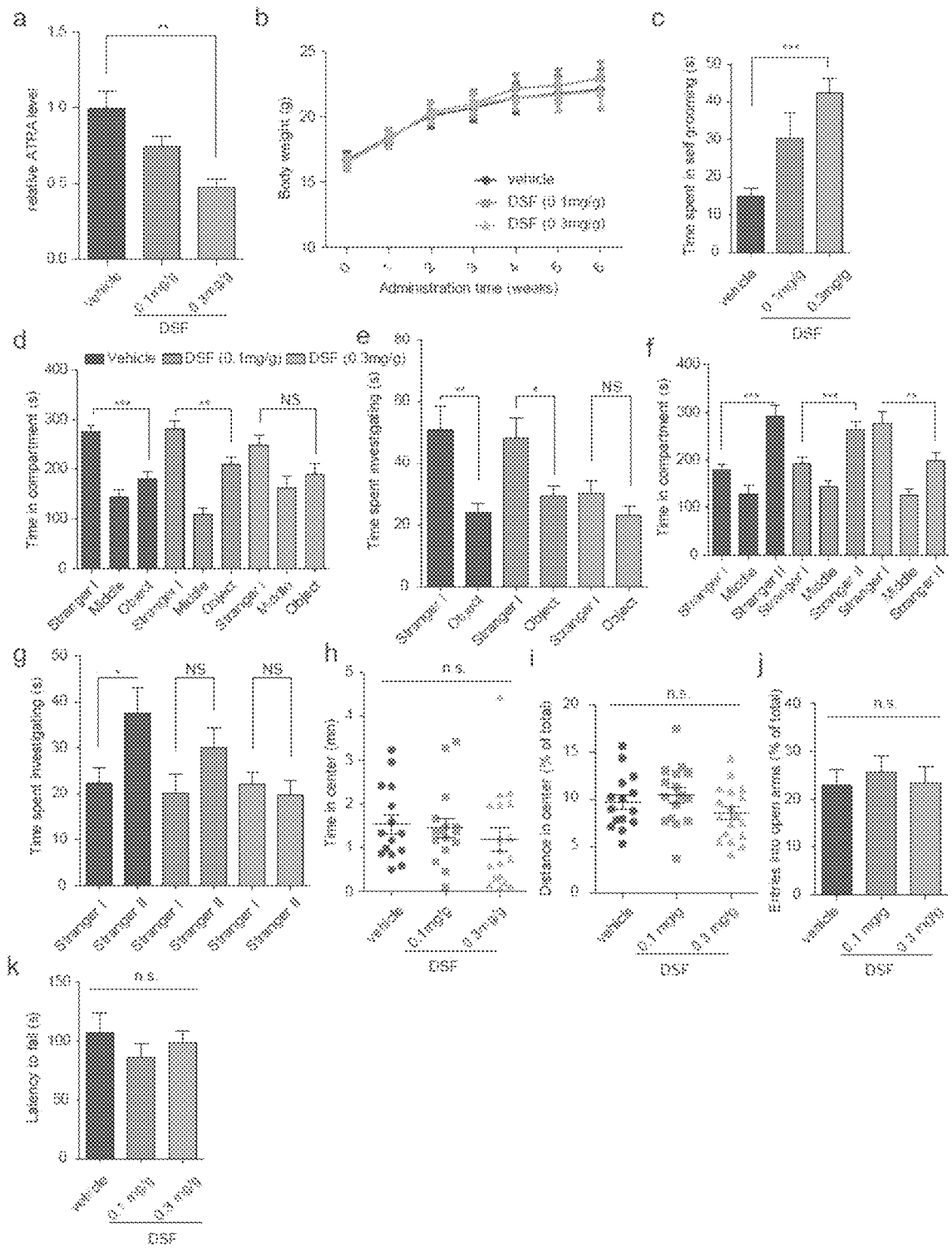
FIG. 9 shows that oral administration of the ALDH1A inhibitor DSF to mice induced an ASD-like phenotype. (a) Mice were orally administered with a solvent or different doses of DSF (0.1 or 0.3 mg/g) for 6 weeks, and the relative ATRA content was determined by HPLC-MS/MS method and corrected with the control group. (b) There were no significant differences in body weight between the different groups of mice. Solvent group (n=10), DSF (0.1 mg/g, n=9), DSF (0.3 mg/g, n=12). (c) Comparison of the time of self-grooming in three groups of mice. (d) Comparison of the residence time in the three groups of mice with unfamiliar mice, in the middle chamber, and in the article chamber. (e) Comparison of the communication time between each of the three groups of mice and strange mice or articles. (f) Comparison of the residence time of mice in the unfamiliar mouse I chamber, the middle chamber, and the unfamiliar mouse II chamber. (g) Comparison of communication time of the three groups of mice with the strange mouse I and the strange mouse II. (h-i) Comparison of residence time in the center of the open field and the ratio of center distance to movement distance for mice gastrically administered with a solvent or 0.1/0.3 mg/g. (j) Comparison of the proportion of number of times of entering the open arm in the elevated cross test in different groups. (k) Comparison of the residence time of different groups of mice before dropping in the rotating rod test. The data were presented as mean and variance. *, P<0.05, , P<0.01, *, P<0.001, NS, no significant difference; (e, g) two-tailed t-test, (a-d, f) one-way ANOVA Bonferroni post-hoc test. c-g, vehicle group (n=15), DSF (0.1 mg/g, n=17), and DSF (0.3 mg/g, n=19).

Example 9 Abnormal Regulation of RA on Homeostasis Caused by Compounds Induces the Autism Phenotypes in Mice To demonstrate whether inhibition of ALDH1A activity alone was sufficient to induce autism phenotype in mice, four-week aged wild-type C57BL/6 mice were orally administered with an Aldh1a inhibitor, disulfiram (DSF). The administration time was lasted for six weeks, and the doses were 0.1 or 0.3 mg/g, respectively, and it was administered every other day. Six weeks after DSF administration, the mouse brain was taken and the ATRA level was detected by HPLC-MS/MS method (Kane et al., 2010). As shown in FIG. 9a, the level of ATRA in the brain tissue of mice administered with DSF for six weeks decreased by 30% (0.1 mg/g dose) and 60% (0.3 mg/g dose), respectively, as compared to the solvent group. This indicated that administration of DSF could inhibit ATRA synthesis in the mouse brain in a dose-dependent manner. Meanwhile, by measuring the body weight of the mice weekly, there was no significant difference in body weight between the groups (FIG. 9b). This suggested that the DSF dose in the experiment did not cause any significant toxic effects in mice.

Next, mice having DSF administration for six weeks were subjected to a double-blind behavioral test. As shown in FIG. 9c, in the self-grooming experiment, the time of self-grooming in DSF-administered mice was significantly doubled (30 seconds, 0.1 mg/g dose) and tripled (42 seconds, 0.3 mg/g dose) as compared to the solvent group (15 seconds). In the three-chamber social experiment, the mice in the solvent group spent significantly more time on interacting with the social mice than with the non-social subjects; however, there was no such obvious trend in the 0.1 mg/g DSF-administered mice (FIG. 9d-e). Also, in the 0.3 mg/g DSF-administered mice, there was no difference between the time spent on interaction with social mouse and the time spent on interaction with non-social articles (FIG. 9d-e). In terms of social novelty, the 0.3 mg/g DSF administration group increased the time spent in the chamber of familiar social mouse by 50% as compared to the solvent group, while the time staying in the chamber of strange social mouse was reduced by 30% (FIG. 9f-g). As to the time of communication with social mice, DSF-administered mice were also completely indistinguishable in communication with familiar mice or with unfamiliar mice. In conclusion, the autistic phenotype of mice was significantly demonstrated after the homeostasis regulation of RA was inhibited by the compound.

Meanwhile, the effects of DSF administration on mice were also evaluated from other behavioral perspectives. In the open field experiment, there was no difference in the time between the three groups staying in the middle area and the distance of the movement (FIG. 9h-i). In the elevated cross maze experiment, there was no significant difference in the number of times entering the open arm as a percentage of all arm entry in three groups of mice (FIG. 9j). These two results clearly showed that the dose of DSF in this study did not affect the anxiety or exploratory behavior of the mice. Meanwhile, the rotating rod experiment also showed that the administration of DSF did not affect the sport ability of the mice (FIG. 9k). These behavioral experiments also reflected that DSF-induced autism phenotype in mice was not caused by its chemical side effects, which was consistent with previous data of mouse body weight (FIG. 9b).

In conclusion, the inhibition of the homeostasis (or steady-state) regulation of RA by the compound could cause the appearance of autism phenotype in mice, and again it emphasized the importance of UBE3A overactivation which could cause ubiquitination of ALDH1A, thereby downregulating RA levels in the etiology of autism.

SUMMARY AND DISCUSSION (1) UBE3A binds to and ubiquitinates ALDH1A2, thereby inhibiting the dehydrogenase activity of ALDH1A2. Similarly, it has been shown that other family members of ALDH1A, such as ALDH1A1 and ALDH1A3, are substrates for UBE3A.

(2) Autism-associated UBE3A overactivation can down-regulate RA levels in cells, thereby affecting RA signaling pathways. It particularly suggests its role in regulating synaptic scaling in neuronal cells.

(3) Overexpression of UBE3A in the PFC region of mouse brain can trigger autism phenotype and the disease phenotype can be can be alleviated by compensation of RA. This can be directly extended to the clinical treatment of human autism.

(4) DSF, a compound inhibitor of ALDH1A, can cause a decrease in RA levels in mice, and can also induce a similar autism phenotype in mice.

(5) This study can expand to the clinical diagnosis of autism in human, and provide novel diagnostic and therapeutic targets for autism. Whether the level of RA and its upstream regulation should be included in the diagnosis tools of autism. It is also possible to screen out and develop drugs for treating autism according to the invention.

(6) Meanwhile, the present invention can also be used to screen for the risk of autism in the offspring caused by the side effects of taking medicines and daily chemicals in pregnant women (as well as the side effects of taking medicines and daily chemicals in infants and young children). It is expected to develop an effective clinical evaluation or diagnosis tool.

(7) A cell model for real-time monitoring of retinoic acid levels was also established. High-throughput screening techniques were used to screen FDA-approved commercial drugs, and several drugs capable of interfering with retinoic acid levels were identified and subjected to future verification, and the verification results were completely as expected. Animal experiments are currently conducting to verify whether these drugs will experimentally induce autism in the offsprings.

In summary, the present invention discloses for the first time that UBE3A can bind to, ubiquitinate and modify ALDH1A family proteins via a non-proteasome degradation way, thereby inhibiting the synthesis of RA and down-regulating the intracellular RA homeostasis. In cultured primary neuron cells, blockage of neuronal activity causes rapid generation of RA, which regulates the process of synaptic scaling of neurons. However, excessive activation of UBE3A interferes homeostasis regulation of RA by blocking the formation of RA. It is also found in mice behavioral studies that overexpression of UBE3A or administration of ALDH I A inhibitor of disulfiram (DSF) can induce autism phenotype. Therefore, there is a correlation between UBE3A overactivation and the autism phenotype. However, since UBE3A has a wide range of physiological effects, it is not appropriate to directly inhibit UBE3A, which may cause some other side effects. Based on the findings of the present invention, targets, medicines, and therapeutic means for preventing and/or treating autism without intervention or intervention of UBE3A are provided.

All references mentioned in the present invention are incorporated herein by reference, as each of them is individually cited herein by reference. Further, it should be understood that, after reading the above contents, the skilled person can make various modifications or amendments to the present invention. All these equivalents also fall into the scope defined by the pending claims of the subject application.

REFERENCES

1. Keren-Kaplan, T. et al. Synthetic biology approach to reconstituting the ubiquitylation cascade in bacteria. The EMBO Journal 31, 378-390 (2012).
2. Kumar, S., Talis, A. L. & Howley, P. M. Identification of HHR23A as a substrate for E6-associated protein-mediated ubiquitination. J Biol Chem 274, 18785-92 (1999).
3. Zaaroor-Regev, D. et al. Regulation of the polycomb protein Ring1B by self-ubiquitination or by E6-AP may have implications to the pathogenesis of Angelman syndrome. Proc Natl Acad Sci USA 107, 6788-93 (2010).
4. Ansari, T., Brimer, N. & Vande Pol, S. B. Peptide Interactions Stabilize and Restructure Human Papillomavirus Type 16 E6 To Interact with p53. Journal of Virology 86, 11386-11391 (2012).
5. Storms, R. W. et al. Isolation of primitive human hematopoietic progenitors on the basis of aldehyde dehydrogenase activity. Proc Natl Acad Sci USA 96, 9118-23 (1999).
6. Chen, L., Lau, A. G. & Sarti, F. Synaptic retinoic acid signaling and homeostatic synaptic plasticity. Neuropharmacology 78, 3-12 (2014).
7. Aoto, J., Nam, C. I., Poon, M. M., Ting, P. & Chen, L. Synaptic signaling by all-trans retinoic acid in homeostatic synaptic plasticity. Neuron 60, 308-20 (2008).
8. Han, E. B. & Stevens, C. F. Development regulates a switch between post- and presynaptic strengthening in response to activity deprivation. Proceedings of the National Academy of Sciences 106, 10817-10822 (2009).
9. Stoner, R. et al. Patches of disorganization in the neocortex of children with autism. N Engl J Med 370, 1209-19 (2014).
10. Chow, M. L. et al. Age-dependent brain gene expression and copy number anomalies in autism suggest distinct pathological processes at young versus mature ages. PLoS Genet 8, e1002592 (2012).
11. Kane, M. A. & Napoli, J. L. Quantification of endogenous retinoids. Methods Mol Biol 652, 1-54 (2010).
12. Xia, K. et al. Common genetic variants on 1p13.2 associate with risk of autism. Molecular Psychiatry 19, 1212-1219 (2013).
13. Nava, C. et al. Prospective diagnostic analysis of copy number variants using SNP microarrays in individuals with autism spectrum disorders. European Journal of Human Genetics 22, 71-78 (2013).
14. Anderson, M. A. & Gusella, J. F. Use of cyclosporin A in establishing Epstein-Ban virus-transformed human lymphoblastoid cell lines. In vitro 20, 856-8 (1984).
15. Xu, J. Preparation, Culture, and Immortalization of Mouse Embryonic Fibroblasts. Curr Protoc Mol Biol. 70, 28.1.1-28.1.8 (2005).
16. Hsu, P. D. et al. DNA targeting specificity of RNA-guided Cas9 nucleases. Nat Biotechnol 31, 827-32 (2013).
17. Aoto, J., Nam, C. I., Poon, M. M., Ting, P. & Chen, L. Synaptic signaling by all-trans retinoic acid in homeostatic synaptic plasticity. Neuron 60, 308-20 (2008).
18. Kane, M. A. & Napoli, J. L. Quantification of endogenous retinoids. Methods Mol Biol 652, 1-54 (2010).
19. Sztainberg, Y. et al. Reversal of phenotypes in MECP2 duplication mice using genetic rescue or antisense oligonucleotides. Nature (2015).

The invention claimed is:

1. A method of treating or preventing autism, which comprises a step of administering to a subject in need thereof a therapeutic agent which promotes production of retinoic acid or decreases degradation of retinoic acid wherein the therapeutic agent comprises a polypeptide or an antibody or a compound capable of blocking binding of UBE3A, and ALDH1A.

2. The method of claim 1, wherein the ALDH1A is selected from the group consisting of ALDH1A1, ALDH1A2, ALDH1A3, and combinations thereof.

3. The method of claim 1, wherein the therapeutic agent is administered in a pharmaceutical composition.

4. The method of claim 3, wherein the pharmaceutical composition comprises: (a) a first active ingredient selected from the group consisting of clotrimazole, montelukast, and montelukast sodium; and (b) a second active ingredient which is the therapeutic agent.

5. The method of claim 1, which comprises administering to a subject in need thereof a pharmaceutical combination, wherein the pharmaceutical combination comprises:
- (a) a first pharmaceutical composition comprising a pharmaceutically acceptable carrier and a first active ingredient selected from the group consisting of clotrimazole, montelukast, and montelukast sodium; and
- (b) a second pharmaceutical composition comprising a pharmaceutically acceptable carrier and a second active ingredient which is the therapeutic agent.

6. The method of claim 1, wherein the subject is administered a safe and effective amount of a second pharmaceutical composition before, during and/or after the administration of the first active pharmaceutical composition.

* * * * *

SEQUENCE LISTING

<160> NUMBER OF SEQ ID NOS: 11

<210> SEQ ID NO 1
<211> LENGTH: 25
<212> TYPE: DNA
<213> ORGANISM: Artificial sequence
<220> FEATURE:
<223> OTHER INFORMATION: Primer

<400> SEQUENCE: 1
caccgagcac aaaactcatt cgtgc            25

<210> SEQ ID NO 2
<211> LENGTH: 25
<212> TYPE: DNA
<213> ORGANISM: Artificial sequence
<220> FEATURE:
<223> OTHER INFORMATION: Primer

<400> SEQUENCE: 2
aaacgcacga atgagttttg tgctc            25

<210> SEQ ID NO 3
<211> LENGTH: 21
<212> TYPE: DNA
<213> ORGANISM: Artificial sequence
<220> FEATURE:
<223> OTHER INFORMATION: Primer

<400> SEQUENCE: 3
aggtcggtgt gaacggattt g            21

<210> SEQ ID NO 4
<211> LENGTH: 19
<212> TYPE: DNA
<213> ORGANISM: Artificial sequence
<220> FEATURE:
<223> OTHER INFORMATION: Primer

<400> SEQUENCE: 4
ggggtcgttg atggcaaca            19

<210> SEQ ID NO 5
<211> LENGTH: 20
<212> TYPE: DNA
<213> ORGANISM: Artificial sequence
<220> FEATURE:
<223> OTHER INFORMATION: Primer

<400> SEQUENCE: 5
aaccaccgag gaaggatacc            20

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
cgttgaggcg ttctgattca            20

<210> SEQ ID NO 7
<211> LENGTH: 23
<212> TYPE: DNA
<213> ORGANISM: Artificial sequence

```
<220> FEATURE:
<223> OTHER INFORMATION: Primer

<400> SEQUENCE: 7
ttctcctgtt ttatggggac tga                                          23

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
ccctacccga aatgcactgt                                              20

<210> SEQ ID NO 9
<211> LENGTH: 25
<212> TYPE: PRT
<213> ORGANISM: Artificial sequence
<220> FEATURE:
<223> OTHER INFORMATION: peptide-1

<400> SEQUENCE: 9

Ala Ser Arg Met Lys Arg Ala Ala Ala Lys His Leu Ile Glu Arg Tyr
1               5                   10                  15

Tyr His Gln Leu Thr Glu Gly Cys Gly
            20                  25

<210> SEQ ID NO 10
<211> LENGTH: 22
<212> TYPE: PRT
<213> ORGANISM: Artificial sequence
<220> FEATURE:
<223> OTHER INFORMATION: peptide-2

<400> SEQUENCE: 10

Asn Asn Ala Ala Ala Ile Lys Ala Leu Glu Leu Tyr Lys Ile Asn Ala
1               5                   10                  15

Lys Leu Cys Asp Pro His
            20

<210> SEQ ID NO 11
<211> LENGTH: 30
<212> TYPE: PRT
<213> ORGANISM: Artificial sequence
<220> FEATURE:
<223> OTHER INFORMATION: peptide-3

<400> SEQUENCE: 11

Ala Glu Ala Leu Val Gln Ser Phe Arg Lys Val Lys Gln His Thr Lys
1               5                   10                  15

Glu Glu Leu Lys Ser Leu Gln Ala Lys Asp Glu Asp Lys Asp
            20                  25                  30
```